(12) United States Patent
Bold

(10) Patent No.: US 12,083,318 B1
(45) Date of Patent: Sep. 10, 2024

(54) SYRINGE ASSEMBLY

(71) Applicant: Albert Bold, Phoenixville, PA (US)

(72) Inventor: Albert Bold, Phoenixville, PA (US)

( * ) Notice: Subject to any disclaimer, the term of this patent is extended or adjusted under 35 U.S.C. 154(b) by 0 days.

(21) Appl. No.: 18/545,076

(22) Filed: Dec. 19, 2023

(51) Int. Cl.
*A61M 5/20* (2006.01)

(52) U.S. Cl.
CPC ................. *A61M 5/2033* (2013.01)

(58) Field of Classification Search
CPC ...... A61M 5/2033; A61M 5/502; A61M 5/19; A61M 5/284; A61M 2005/2073; A61M 2005/1787; A61M 5/315; A61M 5/31501; A61M 5/31505; A61M 2005/3112; A61M 5/1782; A61M 5/326; A61M 5/3234; A61M 5/31596; A61M 5/31598; A61M 5/2448; A61B 5/15; A61J 1/2096; A61J 1/20
USPC .......................................................... 604/135
See application file for complete search history.

(56) References Cited

U.S. PATENT DOCUMENTS

| 2,823,674 A * | 2/1958 | Yochem ............ A61M 5/31555 604/210 |
| 3,838,689 A | 10/1974 | Cohen |
| 4,194,505 A * | 3/1980 | Schmitz ............... A61M 5/2033 604/196 |
| 4,702,737 A | 10/1987 | Pizzino |
| 5,281,198 A * | 1/1994 | Haber .................... A61J 1/2093 604/209 |
| 2011/0087173 A1 | 4/2011 | Sibbitt, Jr. |
| 2011/0224610 A1* | 9/2011 | Lum ................... A61M 5/3145 141/2 |
| 2015/0320935 A1* | 11/2015 | Dungar ............... A61M 5/3234 604/91 |
| 2022/0339365 A1* | 10/2022 | Yu ....................... A61M 5/3155 |

* cited by examiner

*Primary Examiner* — Michael J Tsai
*Assistant Examiner* — Nidah Hussain
(74) *Attorney, Agent, or Firm* — Barley Snyder

(57) ABSTRACT

A syringe assembly and method of deploying the syringe assembly is provided. The syringe assembly includes a syringe body having a hollow syringe barrel, a needle hub provided at a distal end of the syringe barrel, and a flange assembly provided at a proximal end of the syringe body; and a plunger assembly having a primary plunger assembly and a secondary plunger assembly, the primary plunger assembly having a hollow plunger barrel and being configured to be received and slidingly move within the hollow syringe barrel, the secondary plunger assembly configured to be received and slidingly move within the hollow plunger barrel.

18 Claims, 16 Drawing Sheets

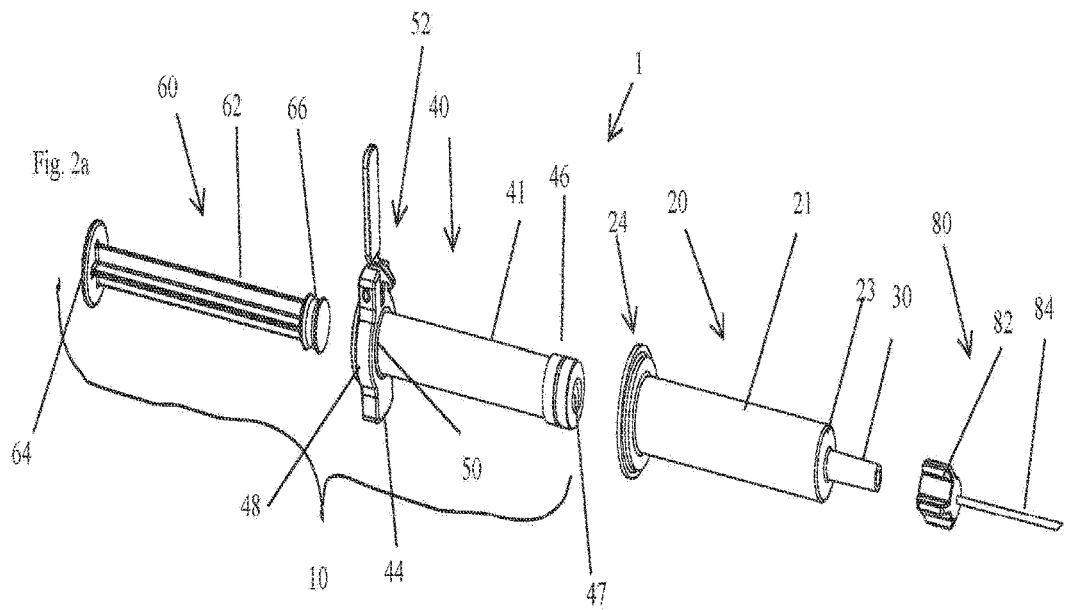
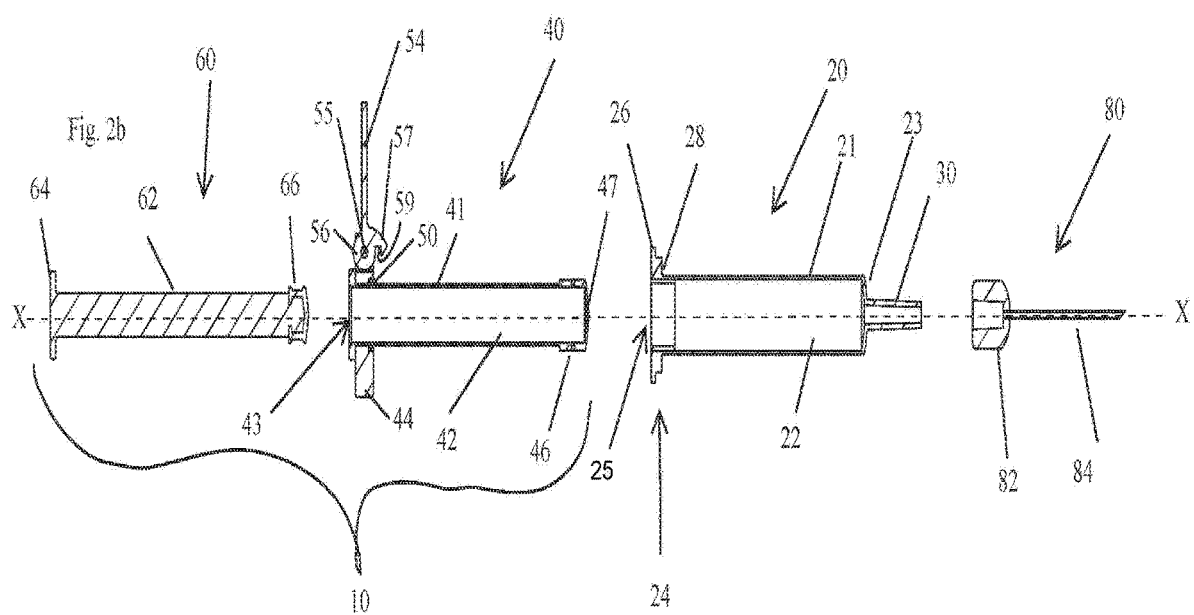

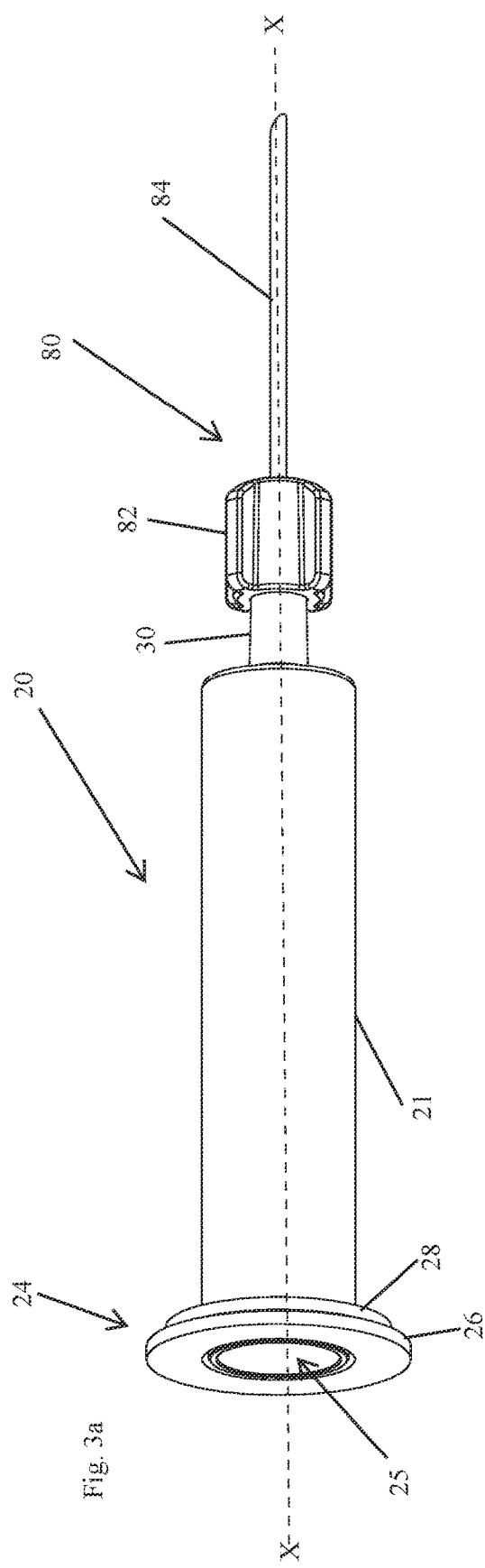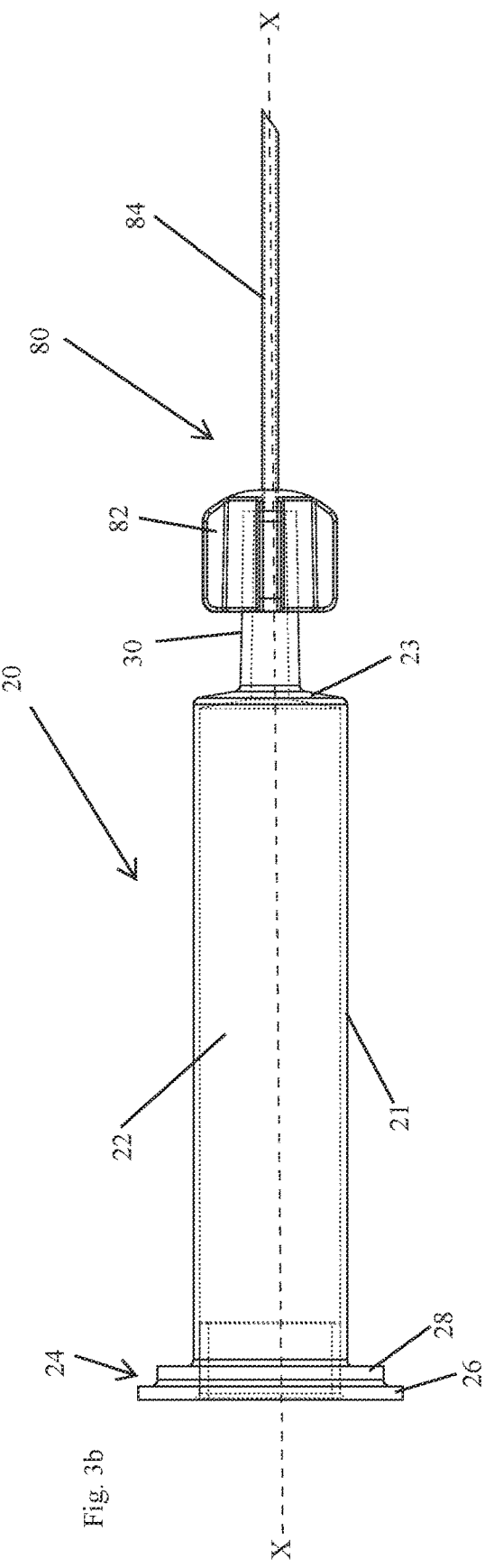

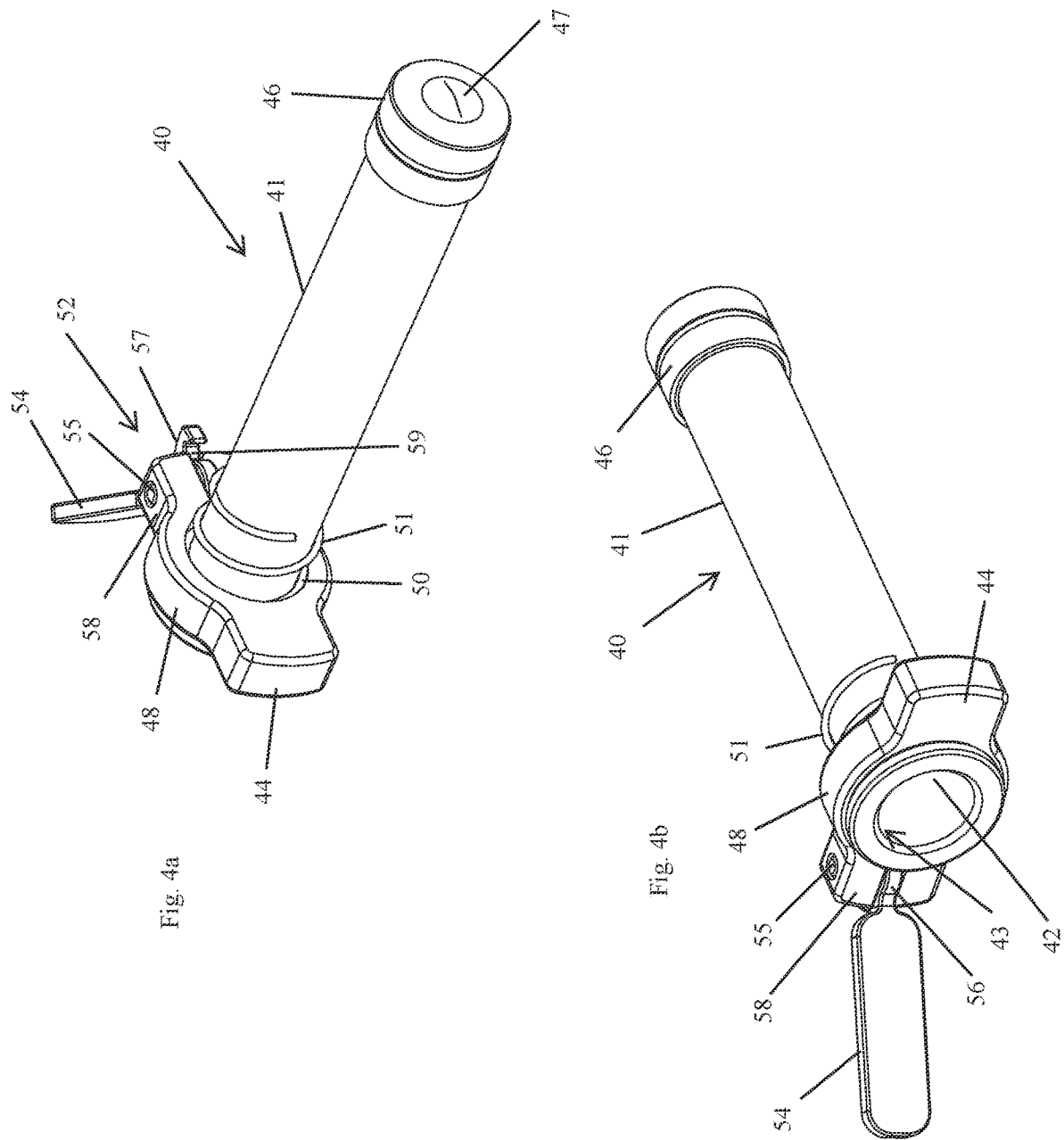

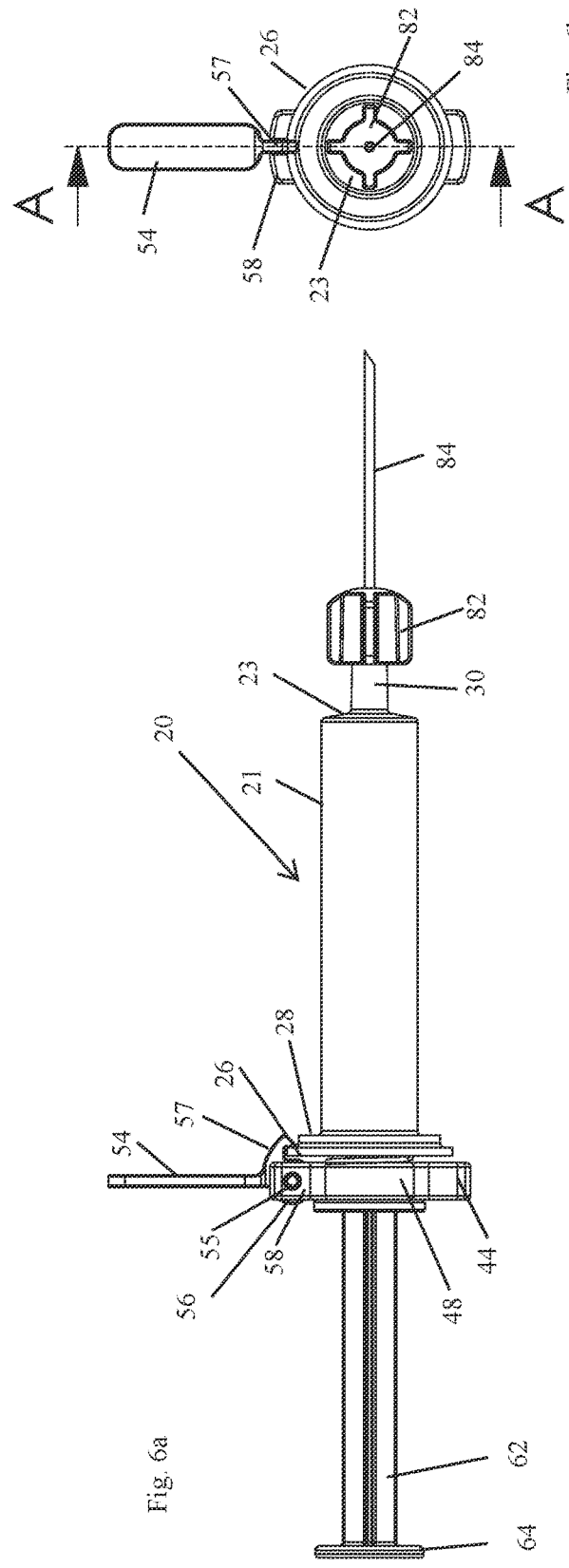
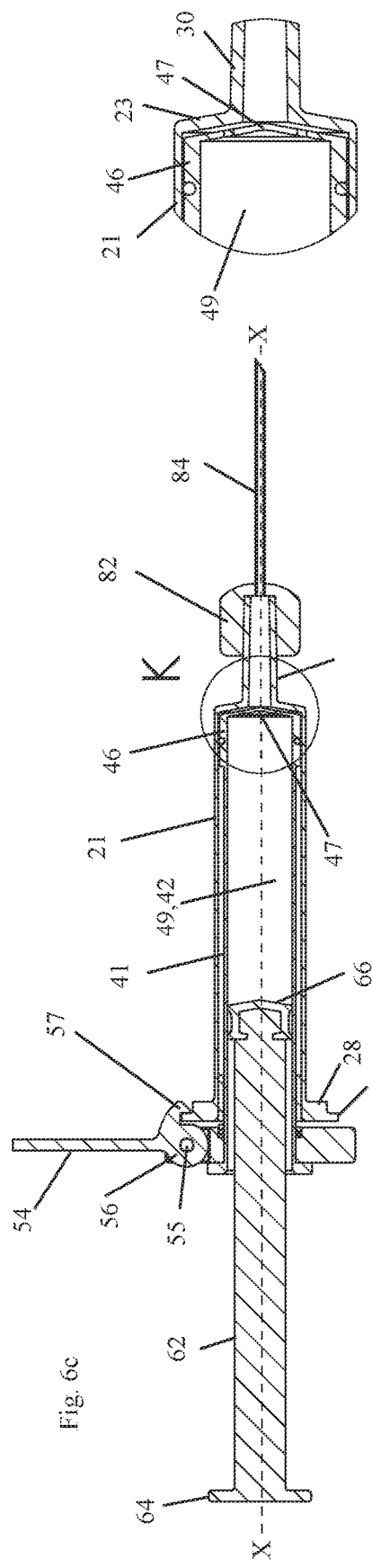

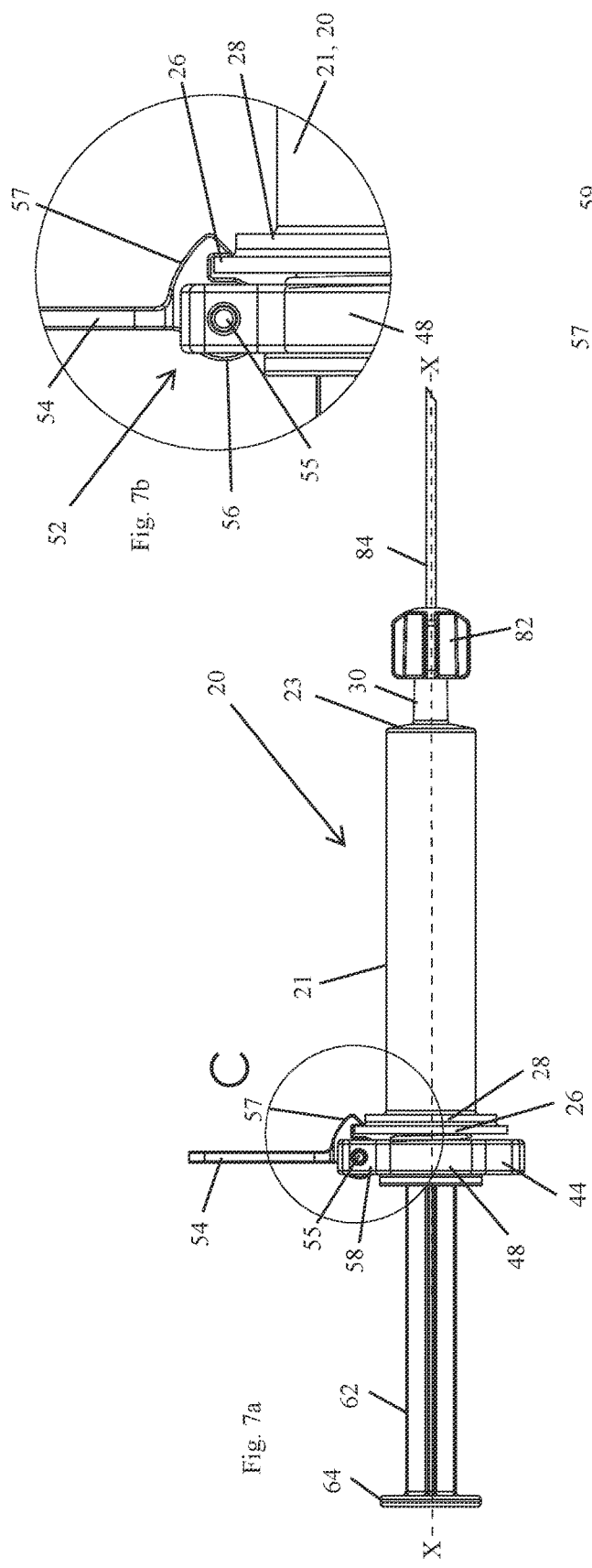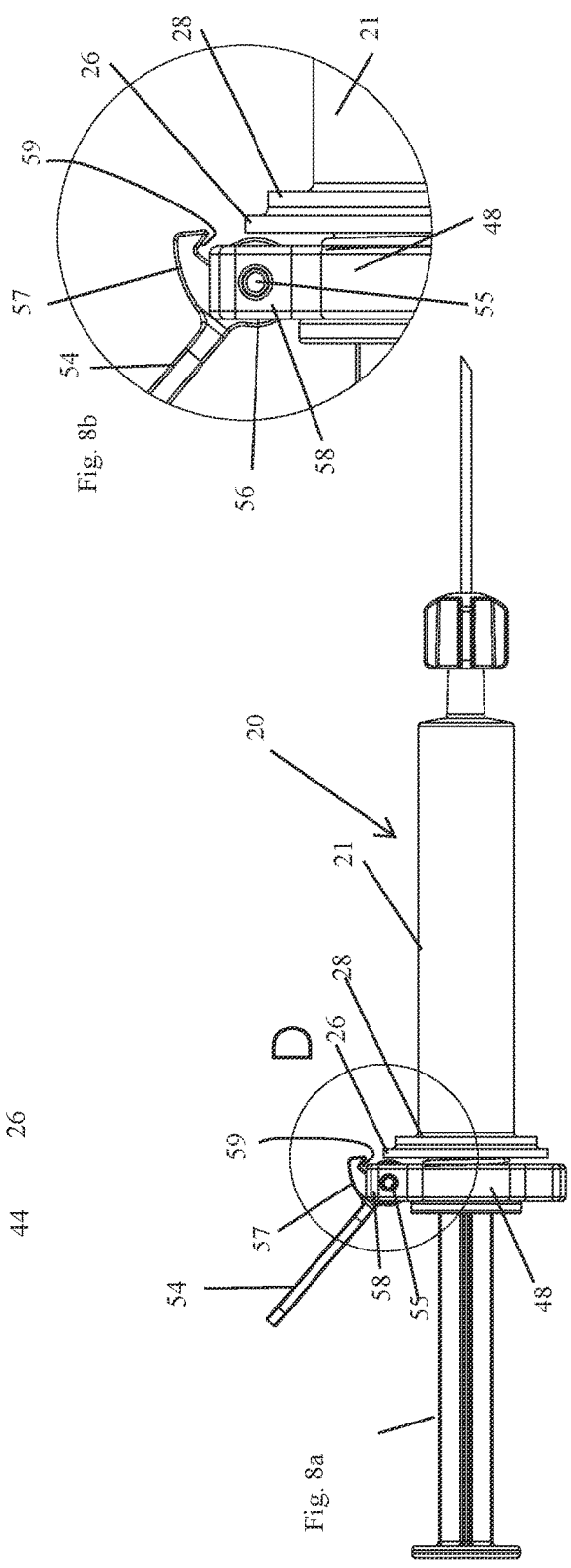

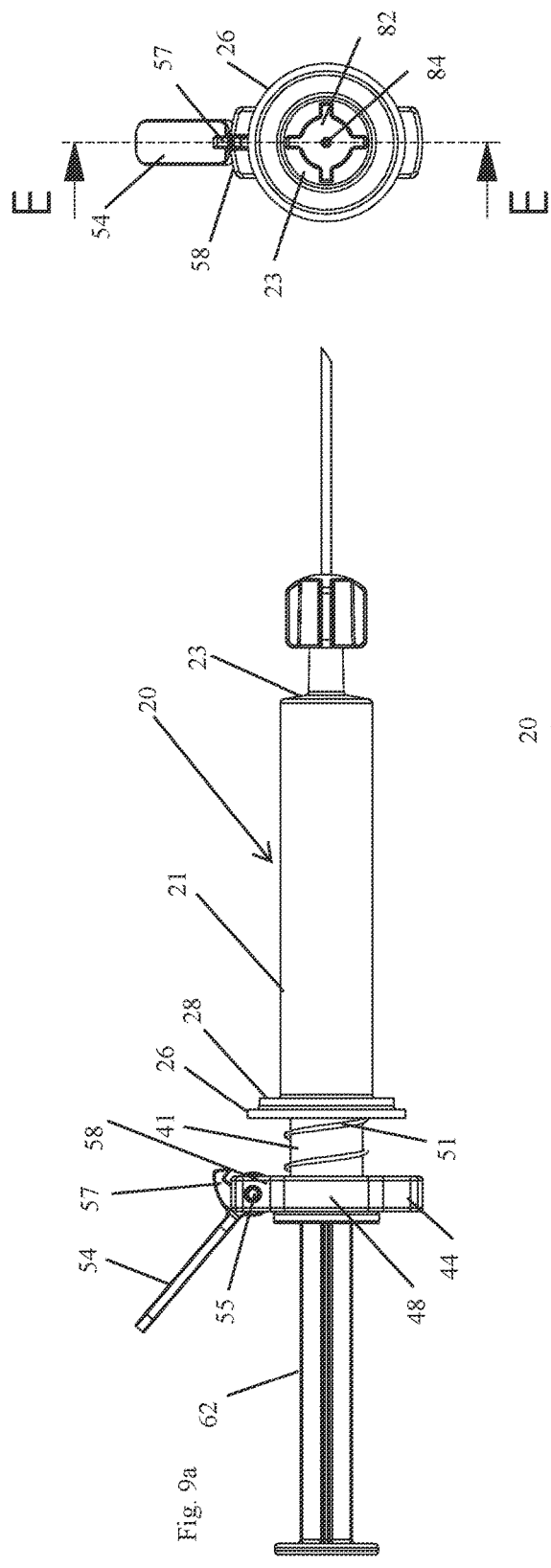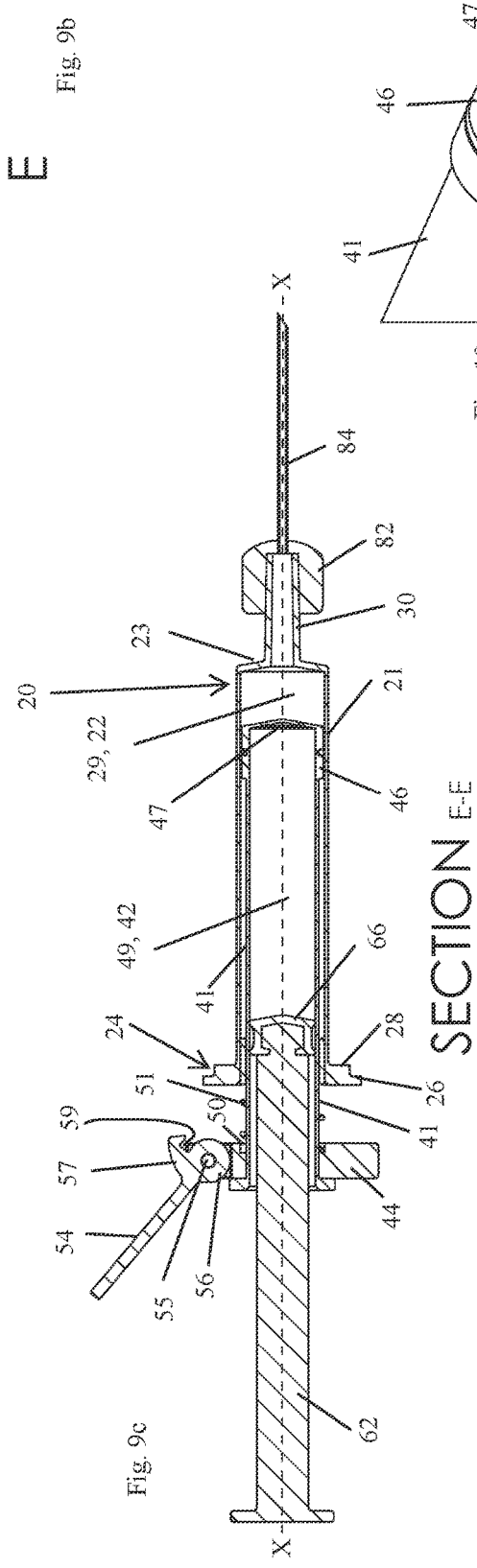

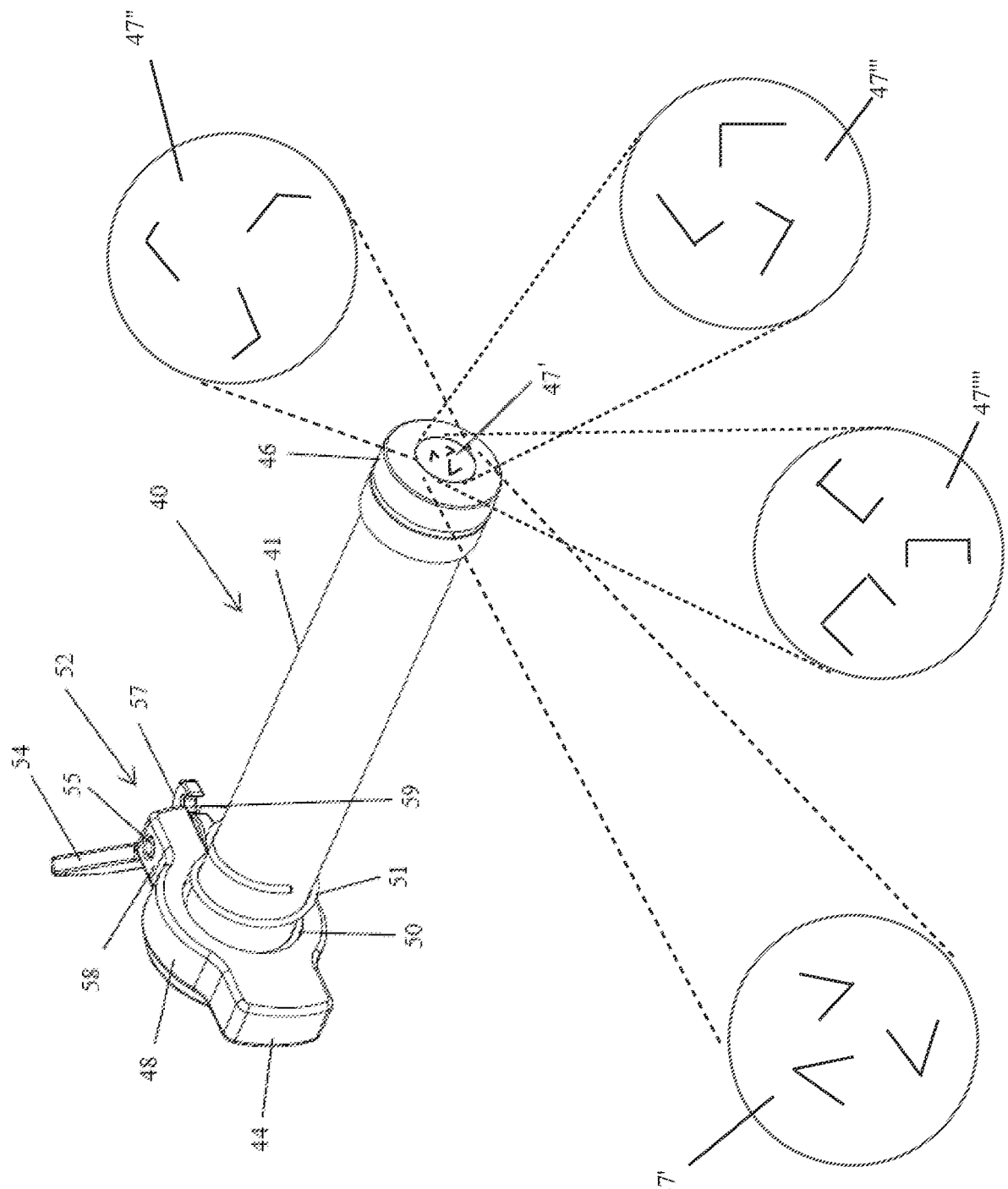

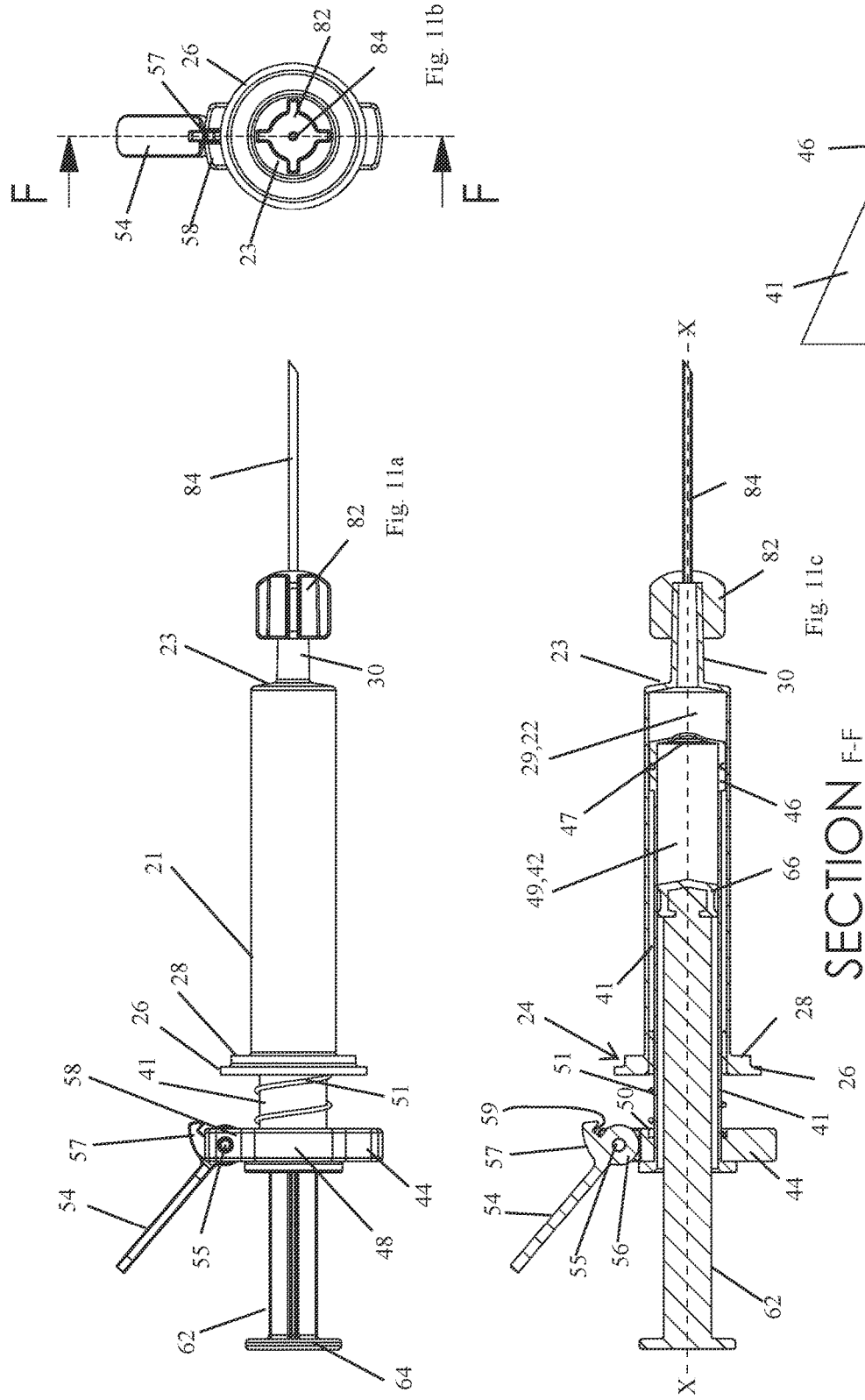

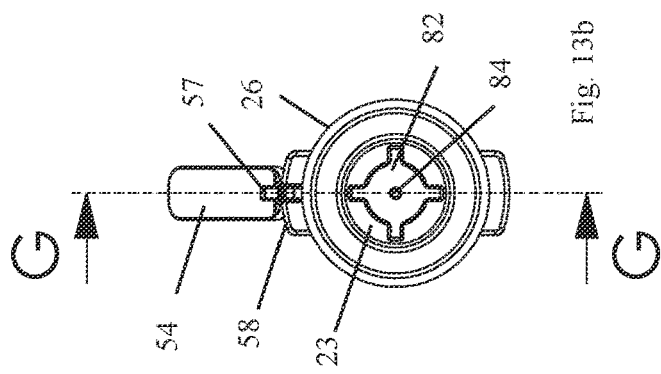
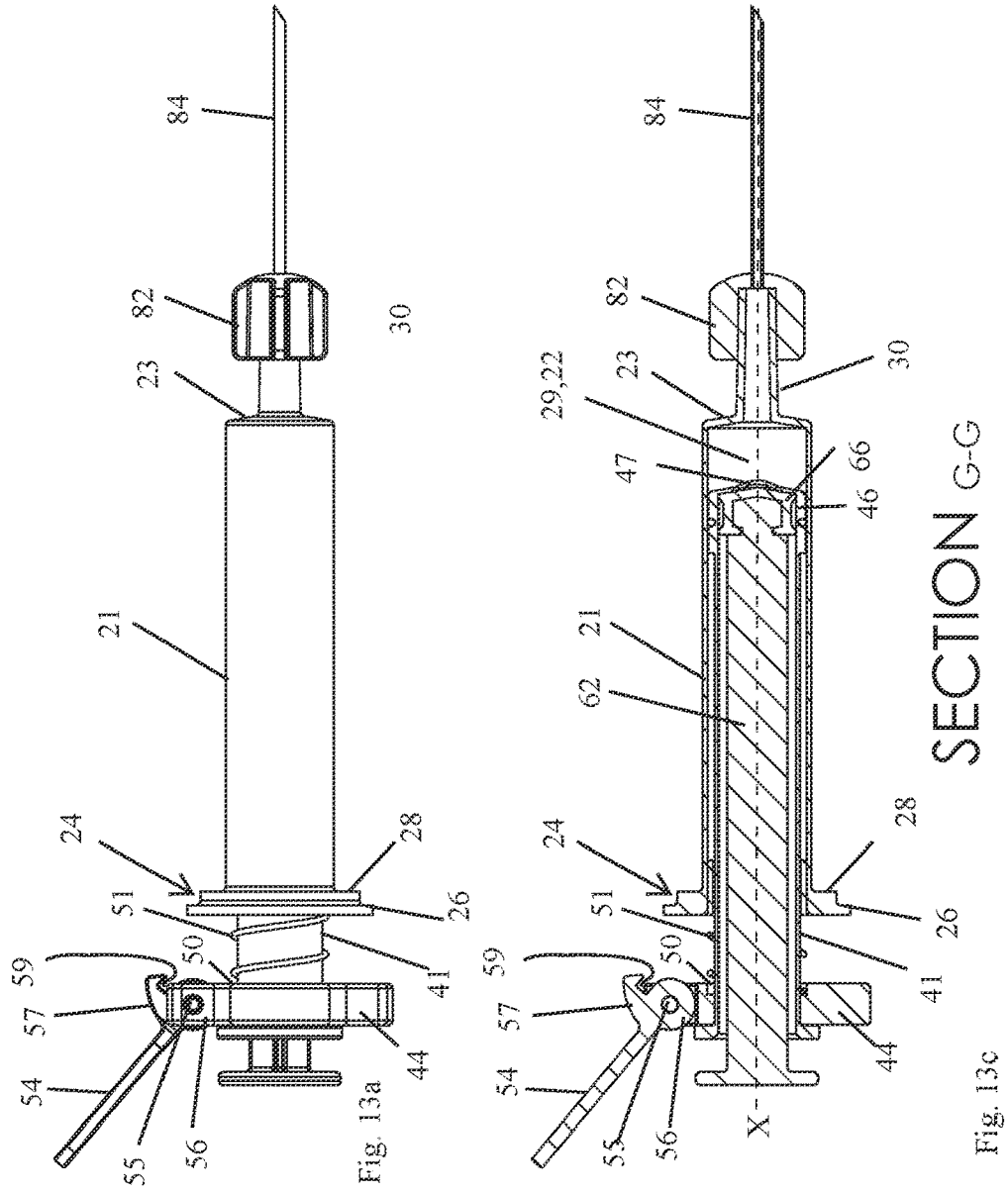

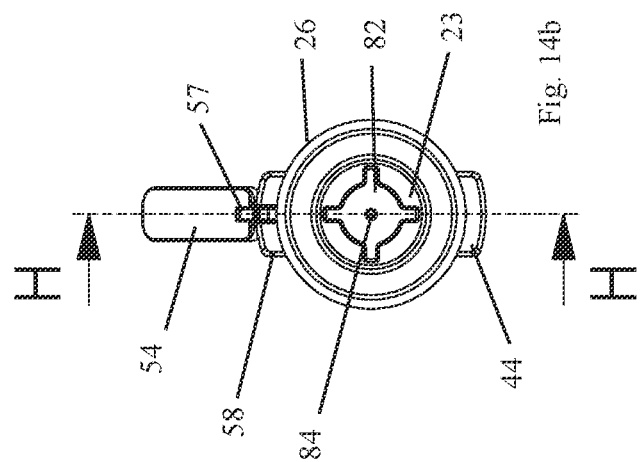
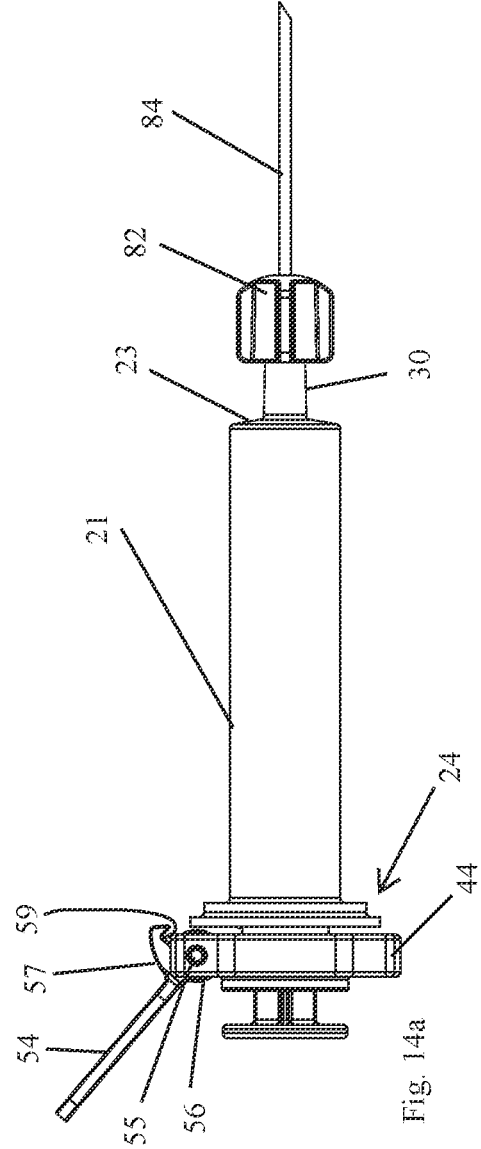
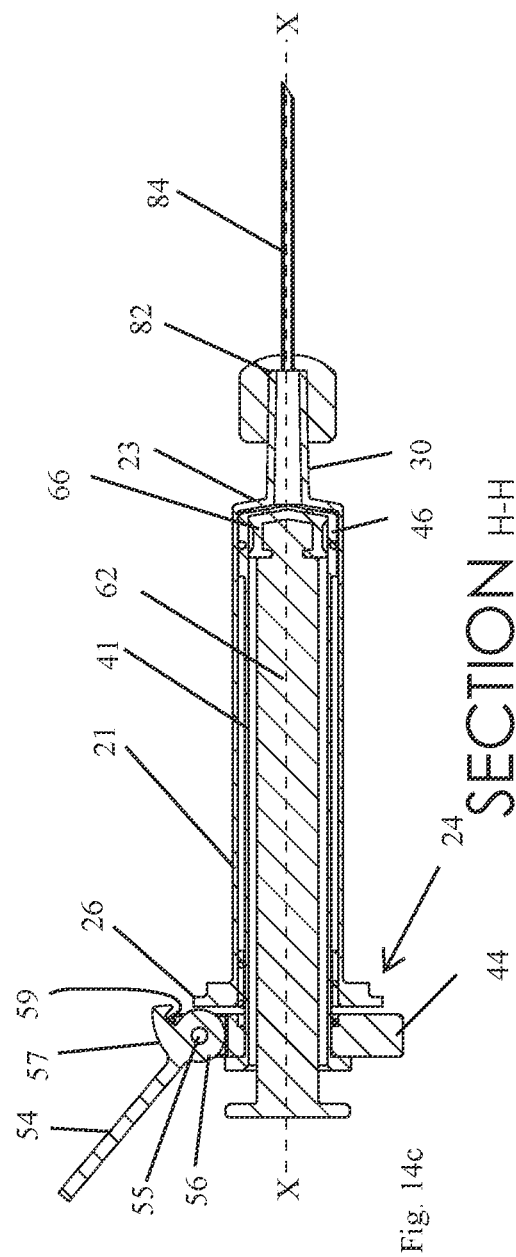

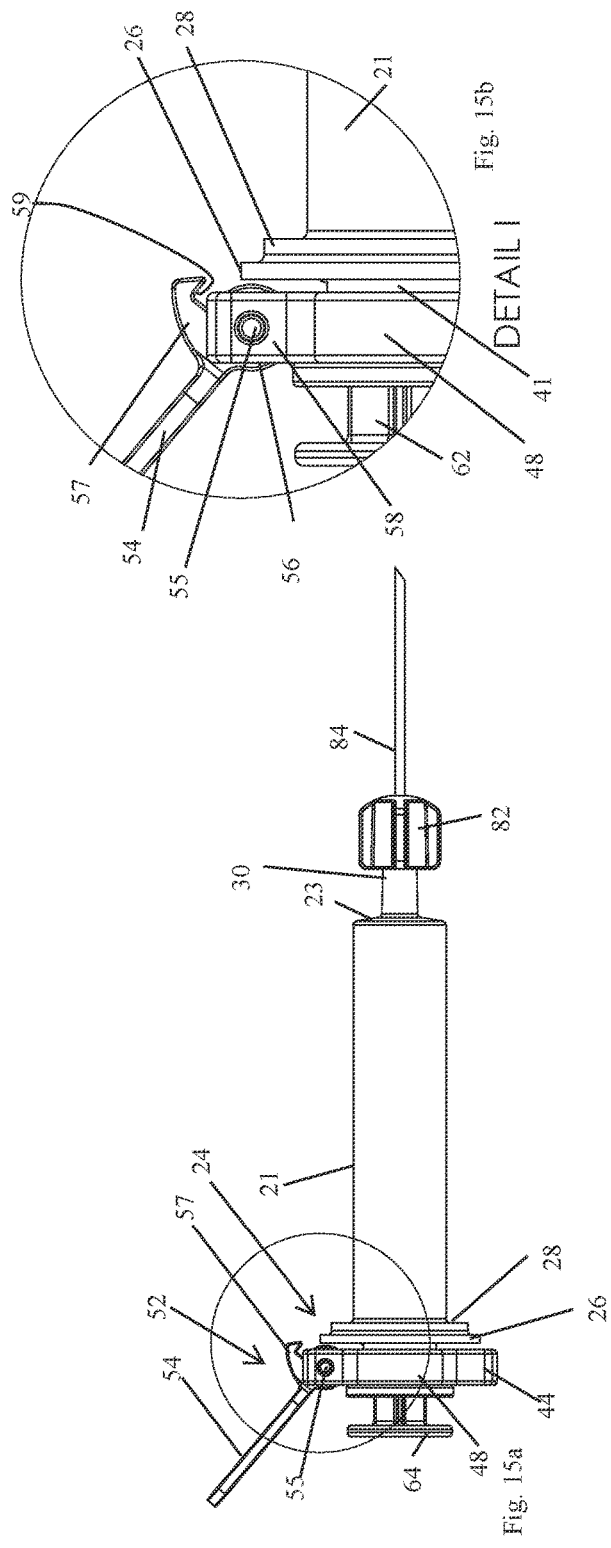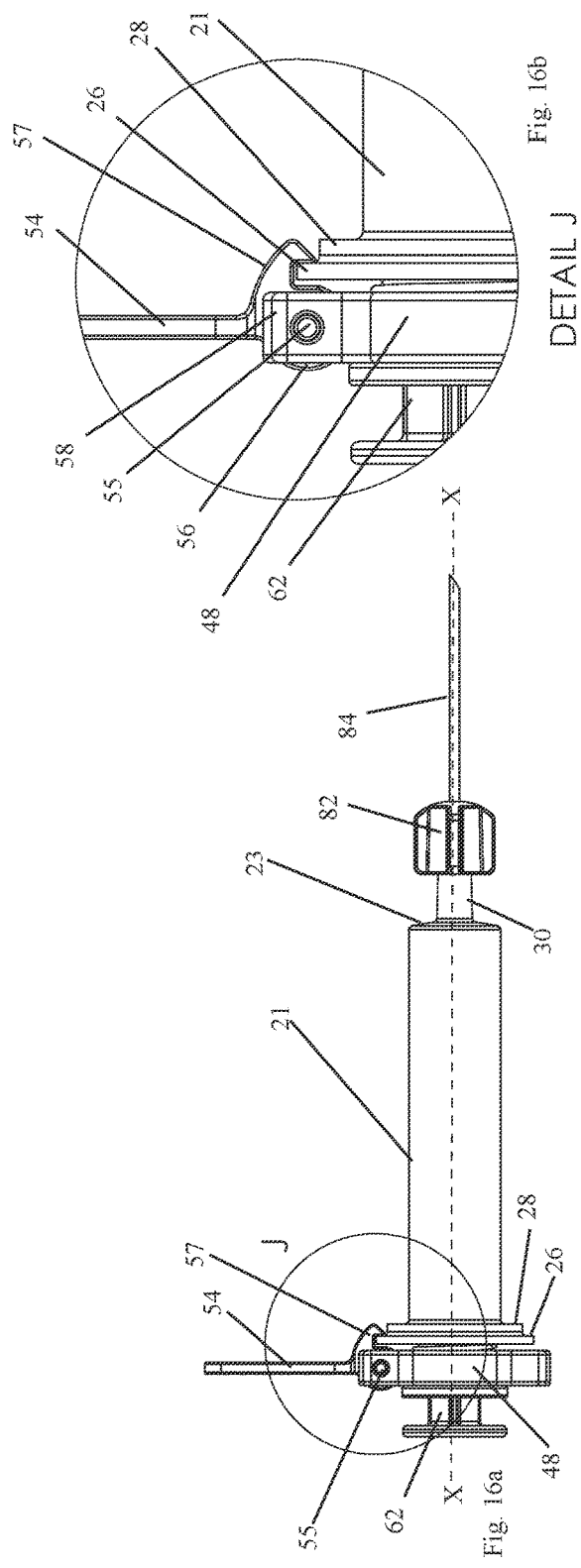

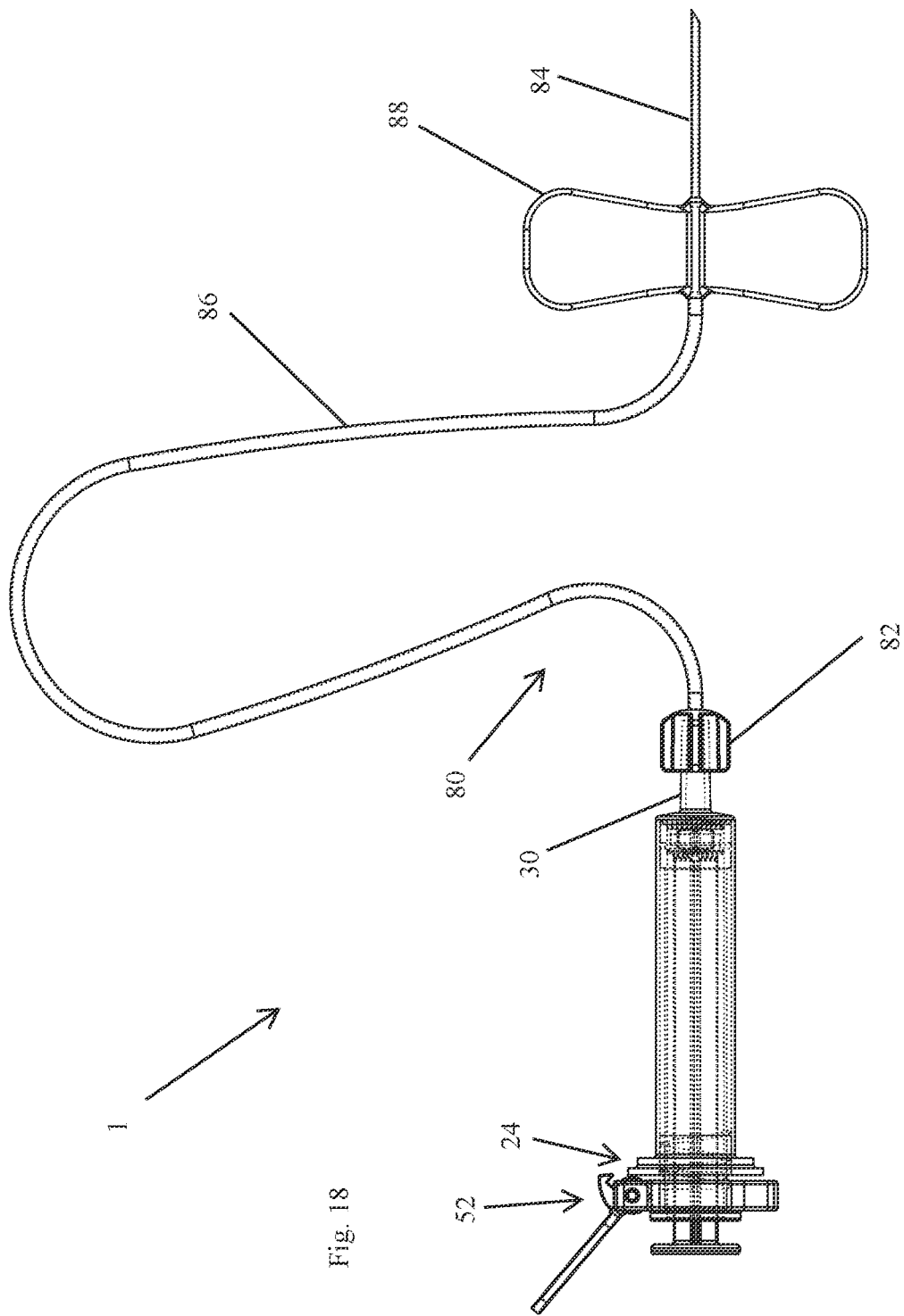

SYRINGE ASSEMBLY

FIELD OF THE INVENTION

This disclosure relates to a device for the administration of a medicament, in particular, this disclosure relates to a syringe device that is capable of being operated with one hand and be caused to aspirate a fluid amount; and for delivering a second fluid to a patient.

BACKGROUND

Medical procedures may require a user to monitor the placement of a needle for a procedure, such as through the use of an ultrasound probe, or where the user may have to manipulate or restrain the tissue from movement as a needle of a syringe is guided to a target site. Such procedures thus may require the operator to use one hand in monitoring the placement of the syringe at the desired target site, and while maintaining control of the tissue or monitoring system, the user may then need to operate the syringe assembly to aspirate an amount of fluid, such as can provide verification of the placement of the needle at the desired location. Thus, there is a need for a syringe that can be guided to a target site, and using one hand, be caused to aspirate an amount of fluid into the syringe assembly.

Accordingly, there is a need for a syringe assembly that can be deployed to position a tip of the needle at a target site, and can allow the user to manipulate the syringe with one hand in order to confirm the positioning by triggering an automatic aspiration of an amount of fluid. Subsequently, the syringe may beneficially be caused to deliver an amount of a second fluid to the target site.

SUMMARY

Accordingly, a system and process for deploying a syringe assembly that can be triggered with one hand to aspirate an amount of fluid, once positioned at target site is provided. Such a syringe assembly may aspirate an amount of fluid when a component is triggered, such as may be possible while maintaining just one hand to manipulate the syringe assembly. The aspirated fluid may provide confirmation of the desired location of the tip of the needle or distal end of the syringe assembly, whereupon deliver of a second fluid may be performed by advancing a second plunger.

In an exemplary embodiment of the invention, there may be provided a syringe assembly having: a syringe body having a hollow syringe barrel, a needle hub provided at a distal end of the syringe barrel, and a flange assembly provided at a proximal end of the syringe body; and a plunger assembly having a primary plunger assembly and a secondary plunger assembly, the primary plunger assembly having a hollow plunger barrel and being configured to be received and slidingly move within the hollow syringe barrel, the secondary plunger assembly configured to received and slidingly move within the hollow plunger barrel.

In an exemplary embodiment, the flange assembly of the syringe body may include a catch and a shoulder. The catch may protrude out from the syringe barrel perpendicularly to a longitudinal axis extending through the center of the syringe body. The shoulder may be provided distal to and adjacent to the catch and joins the flange assembly to the syringe barrel.

In an exemplary embodiment, the primary plunger assembly may have a collar provided at a proximal end of the primary plunger assembly and may have a secondary flange, a biasing device, and a locking assembly, and at a distal end of the primary plunger assembly there may be provided a primary piston and a valve. In an exemplary embodiment, the valve may be a resilient slit valve. The valve may be normally closed but may be caused to resiliently open in response to the sliding movement of the secondary plunger assembly within the hollow plunger barrel.

In an exemplary embodiment, the locking assembly may provide a pivoting body with an actuator and a latch, the pivoting body pivotably mounted to the collar. Actuation of the actuator in a first direction may engage the latch with the catch to secure the primary plunger assembly relative to the syringe body. When the latch is engaged with the catch, the biasing means is compressed between the flange and the collar that are positioned in close proximity. The collar may further provide a recess to receive the biasing means therein when compressed. Actuation of the actuator in a second direction may disengage the latch from the catch to allow sliding movement of the primary plunger assembly relative to the syringe body, when the biasing device is able to transition to an uncompressed state.

In an exemplary embodiment, there is taught the method of delivering a medicament with a syringe assembly, the method comprising the steps of: 1) providing a syringe assembly having a syringe body with a first internal chamber, a needle assembly with a lumen therethrough and in fluid communication with the first internal chamber, a primary plunger assembly with a second internal chamber having a second fluid therein and having a valve located at the distal end of the second internal chamber, the valve being in fluid communication with the first internal chamber, the primary plunger assembly configured to slidingly fit within the first internal chamber; and a secondary plunger assembly configured to slidingly fit within the second internal chamber, and having a biasing device provided in a compressed state positioned between the primary syringe assembly and the syringe body, while a lock assembly remains engaged; 2) directing a tip of the needle assembly positioned on a distal end of the syringe assembly to a target location; 3) disengaging the lock assembly, whereupon the biasing device transitions from a first state characterized by the biasing device being compressed to a second, and uncompressed state, simultaneously urging a proximal directed movement of the primary plunger assembly within the first internal chamber of the syringe body, and causing a first fluid to be drawn into a first fluid chamber within the first internal chamber, and thereby confirming the location of the tip of the needle at the target site; and 4) advancing the secondary plunger assembly in a distal direction to deliver an amount of the second fluid from the second internal chamber through the valve and into the first internal chamber, and further through the lumen of the needle assembly to the target site.

In an exemplary embodiment, the second fluid may be or contain a medicament. In an exemplary embodiment, the biasing device may be a resilient coiled spring positioned between a collar provided at the proximal end of the primary plunger assembly, and a flange assembly provided at a proximal end of the syringe body, the coiled spring being wound about a portion of the primary plunger assembly. The coiled spring may be configured to be releasably compressed into a coiled state having stored energy therein, and the coiled spring is configured to be received within a recess in the collar. The flange assembly may provide a circular catch and shoulder, the shoulder joining the flange assembly to the syringe body, and the circular catch protruding radially out from the shoulder.

BRIEF DESCRIPTION OF THE DRAWINGS

The invention will now be described by way of example with reference to the accompanying figures of which:

FIG. 2a is a partially exploded view of the major components of an exemplary embodiment of the invention;

FIG. 2b is a cross section view of the partially exploded view of FIG. 2a;

FIGS. 3a and 3b are an isolated view of the syringe barrel and needle assembly, provided in a side perspective view, and side view, showing details of internal aspects, respectively, according to an embodiment of the invention;

FIGS. 4a and 4b are perspective views of the primary plunger assembly from opposite perspectives, according to an embodiment of the invention;

FIG. 6a-d depict aspects of an embodiment of the syringe assembly, wherein the primary plunger assembly is locked by the locking assembly to the syringe body, and the secondary plunger assembly is partly inserted into the primary plunger assembly, according to an embodiment of the invention;

FIGS. 7a and 7b show the lock assembly in an engaged state, in a perspective view and in greater detail, respectively, with the secondary plunger remaining in the position depicted in FIG. 6c, according to an exemplary embodiment of the invention;

FIGS. 8a and 8b show the lock assembly in a disengaged state, in a perspective view and in greater detail, respectively, prior to the primary plunger assembly being urged proximally within the syringe body by the biasing device, according to an exemplary embodiment of the invention;

FIGS. 9a-c depict aspects of an embodiment of the syringe assembly, wherein the locking assembly has been released and the primary plunger assembly has been caused to be moved proximally within the syringe body in response to the urging of the biasing device as it returns to an uncompressed state, and the secondary plunger assembly remains partly inserted into the primary plunger assembly, according to an embodiment of the invention;

FIG. 10a depicts a perspective view of the distal portion of the primary plunger assembly, showing the primary piston and valve, with the valve in a closed state, according to an embodiment of the invention;

FIG. 10b depicts a perspective view of the primary plunger assembly having alternative exemplary slit seals, shown in ana closed state, in the exemplary valves, in order to provide directional flow and swirling of fluids within the primary chamber as fluid is ejected from the secondary chamber;

FIGS. 11a-c depict aspects of an embodiment of the syringe assembly, wherein the primary plunger assembly is as provided in FIG. 9a-c, only with the secondary plunger assembly having been manually urged distally within the hollow barrel of the primary plunger assembly, to expel a fluid through the valve, according to an embodiment of the invention;

FIG. 12 depicts a perspective view of the distal portion of the primary plunger assembly, showing the primary piston and valve, with the valve in an open state, according to an embodiment of the invention;

FIGS. 13 a-c depict aspects of an embodiment of the syringe assembly, wherein the primary plunger assembly is as provided in FIG. 9a-c, only with the secondary plunger assembly having been manually urged distally to the maximum extent within the hollow barrel of the primary plunger assembly, and the secondary piston has been advanced to the distal end of the primary plunger assembly, according to an embodiment of the invention;

FIGS. 14 a-c depict aspects of an embodiment of the syringe assembly, wherein the primary plunger assembly and the secondary plunger assembly having both been urged distally to the maximum extent within the syringe body, returning the biasing device to a compressed state, and with the lock remaining disengaged, according to an embodiment of the invention;

FIGS. 15a and 15b depict the lock assembly in a disengaged state, in a perspective view and in greater detail, respectively, with the secondary plunger having been urged fully in a distal direction, and the primary plunger assembly having been urged fully in a distal direction, according to an exemplary embodiment of the invention;

FIGS. 16a and 16b depict the lock assembly returned to an engaged state, in a perspective view and in greater detail, respectively, with the secondary plunger having been urged fully in a distal direction, and the primary plunger assembly having been urged fully in a distal direction, according to an exemplary embodiment of the invention;

FIGS. 17 and 18 depict an exemplary embodiment of the syringe assembly providing a needle assembly that includes a flexible lumen connecting the needle to the connector fitting, such as the winged infusion set shown, with the secondary plunger provided in FIG. 17 fully retracted within the primary plunger assembly, and in FIG. 18, the secondary and primary plunger assemblies are fully urged distally within the syringe body, and positioned for re-engagement of the lock assembly, according to an embodiment of the invention.

DETAILED DESCRIPTION OF THE EMBODIMENTS

Figure 1A:
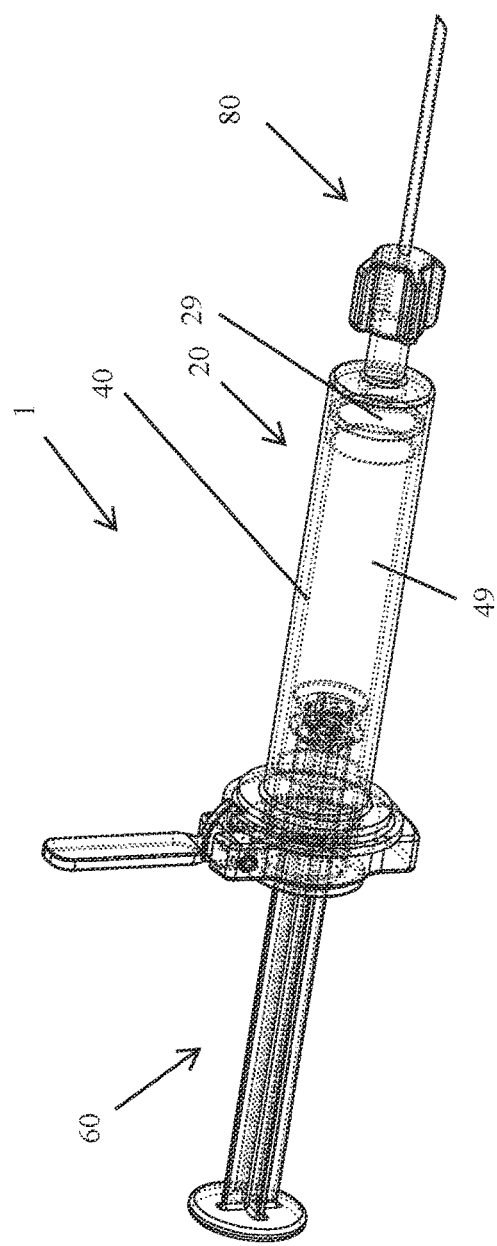
FIGS. 1a and 1b are perspective views of the assembled syringe assembly from opposite perspectives, according to an embodiment of the invention.

The terminology used herein is for the purpose of describing particular embodiments only and is not intended to be limited of the invention. As used herein, the term "and/or" includes any and all combination of the one or more of the associated listed items. As used herein, the singular forms "a", "an", and "the" are intended to include the plural forms as well as the singular forms, unless the context clearly indicates otherwise. It will be further understood the terms "includes" and/or "comprising", when used in this specification, specify the presence of stated features, steps, operations, elements, and/or components, but not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present disclosure is to be considered as an exemplification of the invention and is not intended to limit the invention to the specific embodiments illustrated by the figures or description provided. Other systems, methods, features and advantages of the invention will be or will become apparent to one with skill in the art upon examination of the following figures and detailed description.

With reference to the figures herein, various aspects of a syringe assembly and components thereof, according to an exemplary embodiment of the invention, will be described.

A syringe assembly 1 is provided and in an exemplary embodiment may beneficially be employed in a manner that allows the aspiration of an amount of fluid into the syringe assembly, and then may be actuated to dispense or eject an amount of a medicament, or other fluid from the syringe assembly. The syringe assembly 1, generally provides a syringe body 20, having a plunger assembly 10, and having an orifice at the distal end of the syringe assembly that is in fluid communication with the interior aspects of the syringe assembly. For case of description, the syringe assembly and individual components thereof may each be referred to as having proximal and distal ends. The term "distal" will refer to the leading end of the device while in use, terminating with the narrowed opening at the needle hub 30, or, if present, with the pointed end of the needle. The term "proximal" will refer to the trailing end of the device in use, characterized by having the plunger end, as is known with syringes. As shown in the perspective view of FIG. 1a, the proximal end corresponds to the end of the plunger portion positioned on the left in the depiction, and the distal end corresponds to the pointed end of the needle portion, positioned on the right as illustrated. A reverse perspective view is provided in FIG. 1b. As illustrated, the syringe body 20 is configured to receive at least a portion of the plunger assembly 10 therein, where actuation of the components of the plunger assembly 10 may serve to aspirate and eject a fluid through an opening at the distal end of the syringe assembly 1, as will be discussed.

A partially exploded view of the syringe assembly can be seen with reference to FIG. 2a, and in corresponding cross-section in FIG. 2b. As shown, the syringe assembly 1 generally includes at least the following major components: a syringe body 20, a plunger assembly 10 having a primary plunger assembly 40, a secondary plunger assembly 60. The syringe assembly 1 may optionally include a needle assembly 80, configured to fit onto the distal end of the syringe body 20. As used, and as shown in FIGS. 2a and 2b, the major components of the syringe assembly 1 are generally arranged along a longitudinal axis "X" extending along the radial centerline of the major components. Many of the major components of the syringe assembly are in sliding relationship with each other, to allow longitudinal movement of the plunger assembly components along the longitudinal axis.

The syringe body 20 as shown in FIGS. 2a and 2b, and with reference to the syringe body shown in isolation in the enlarged views of FIGS. 3a, and corresponding cross section view of FIG. 3b, may be a generally tubular barrel 21 structure having a longitudinal axis "X", and an annular sidewall positioned around the longitudinal axis at a syringe body radius, thereby defining an interior chamber 22. The tubular structure provides an internal surface and an external surface. The syringe body 20 may have a flange assembly 24 positioned at the proximal end of, or about the external surface of the sidewall near the proximal end of the tubular barrel 21 structure. Additionally, the tubular barrel structure of the syringe body 20 has an opening for receiving the plunger assembly 10 therethrough, referred to as the primary plunger opening 25, provided at a proximal end of the syringe body. The primary plunger opening 25 is substantially the same diameter as interior of the tubular structure 21 of the syringe body 20. At the distal end of the tubular structure 21 of the syringe body 20, there is provided a needle hub 30 and a distal wall 23. The distal wall serves to largely close off the distal end of the syringe body by bridging a gap existing between the distal end of the tubular structure 21 and the proximal end of the needle hub 30. Thus, the distal wall forms a shoulder provided at the distal end of the syringe body, and may be slightly tapered in profile, or conical in perspective view, or alternatively may be generally planar and provided in a plane perpendicular to the longitudinal axis X. The distal wall 23 largely seals off the distal end of the tubular structure, but for an opening therethrough that is in fluid communication with an interior lumen of the needle hub 30 during the entirety of the use of the device. Thus, the interior lumen of the needle hub 30 will always be in fluid communication with the interior chamber 22 of the syringe body 20, notwithstanding the action of the plunger assembly 10. Only when the interior chamber 22 is emptied by the action of the primary piston 46 being advanced against the distal wall 23, when the primary plunger assembly 40 has been fully urged in a distal direction, would the lumen of the needle hub 30 not be in fluid communication with the interior chamber 22 of the syringe body. As shown, the needle hub may be a protruding tubular structure extending from the center of the distal wall 23 of the syringe body 20, in line with the longitudinal axis of the syringe body. Alternatively, it is contemplated that the needle hub 30 may be eccentrically positioned, and protrude off center from the distal wall at a position other than aligned with the longitudinal axis of the syringe body. The needle hub 30 may be a cylindrical protruding body and may optionally be slightly tapered to provide a friction fit between the needle hub and a needle assembly 80, as will be discussed. Additionally, the needle hub may have any suitable features for securing a needle assembly 80 thereto, including threads, or a keyed connection, as will be familiar to those of skill in the art. The needle hub may further be provided with a protective shroud to protect the engagement features of the needle hub, as are known with luer assemblies, and will be familiar to those of skill in the art. Once the needle assembly 80, if present, is secured on the needle hub 30, the lumen within the needle assembly 80 will be in fluid communication with the interior chamber 22 within the syringe body 20.

The flange assembly 24 may be provided at, or near the proximal end of the syringe body 20 and configured to extend radially outwards (away from the longitudinal axis X) and is configured to provide a surface for user's fingers to engage when operating the syringe, for example, when actuated to expel fluid. As shown, the flange assembly 24 provides a circular catch 26 and a shoulder 28. The catch 26 portion is provided as the outermost rim of the flange assembly 24 and is at the greatest extent of the flange assembly 24 away from the longitudinal axis. Positioned adjacent to the distal surface of the catch 26, the shoulder 28 portion of the flange assembly 24 is provided. The flange assembly 24 provides a grip for resting fingers against, in a manner that is known for the manual operation of syringes for expelling fluid, by operation of the plunger assembly, as will be discussed. It is contemplated that the shoulder 28 need not be a separate component of the flange assembly, such as where the flange is a uniformly shaped disk protruding radially out from the distal end of the syringe body, typically perpendicular to the longitudinal axis. Typically, the user's fingers would rest against the exterior surface of the tubular syringe barrel, and against the distal face of the shoulder when gripping the syringe body 20 for actuating the plunger assembly, as will be discussed.

The catch 26, as can be seen in the cross-section view of FIG. 2b, may feature a protruding profile extending radially out from the shoulder 28. In an embodiment, and as shown in FIG. 3b, the catch 26 has a substantially rectangular profile. The catch 26 may engage a correspondingly shaped latch 57 of a locking assembly 52, as will be discussed. It is recognized that alternative catch designs are possible and may be provided as alternative embodiments, relying on the teachings herein.

In an exemplary embodiment, the syringe body 20 may receive a needle assembly 80 that may be secured to the needle hub 30, through any suitable connection means. As shown, the needle assembly 80 provides a needle, such as a hypodermic needle, having a pointed distal end, and a lumen therethrough, and the proximal end of the needle may be received within a connector fitting 82, that is configured to be secured onto the needle hub 30, and establish a fluid pathway from the lumen of the needle hub to the distal tip of the needle. In this manner, fluid may pass through the needle 84 in either a proximal or distal direction when used to either aspirate, or deliver fluid to or from the interior chamber 22 of the syringe body 20. In an embodiment, the distal tip may be a male luer fitting, and the connector fitting 82 may be a female luer fitting, such that the needle assembly can be reversible secured to the needle hub. It is also contemplated that the syringe assembly 1 may be operated as discussed herein without employing a needle assembly, for applications that do not require the needle to pierce a material for operation of the syringe assembly 1.

The syringe body 20 may be of any suitable construction, including polymer, glass, and metal, or combinations thereof. The components of the syringe body may be a uniform material, or alternatively, multiple materials may be combined for assembling the syringe body; such as where the tubular portion of the syringe barrel 21, distal wall 23, and needle hub 30 are of polymer or glass construction, and at least a portion of the flange assembly 24 may be metal. Where the same material is used for all of the components of the syringe body 20, any suitable manner of manufacturing the syringe body may be employed, such as injection molding, or milling. Where components of the syringe body 20 are provided separately, and joined during manufacture, particularly where dissimilar materials are provided, such as for the flange assembly 24 and the tubular barrel construction, the components may be secured together in any suitable fashion, including through the use of fasteners, threaded elements, adhesives, welding, or friction fit.

As will be familiar to those of skill in the art, a portion of the syringe assembly 1 may be provided with markings, such as graduated markings, that may be provided for monitoring volumes contained in the syringe components, and may be aspirated, and or delivered with the syringe assembly 1.

Figure 5A:
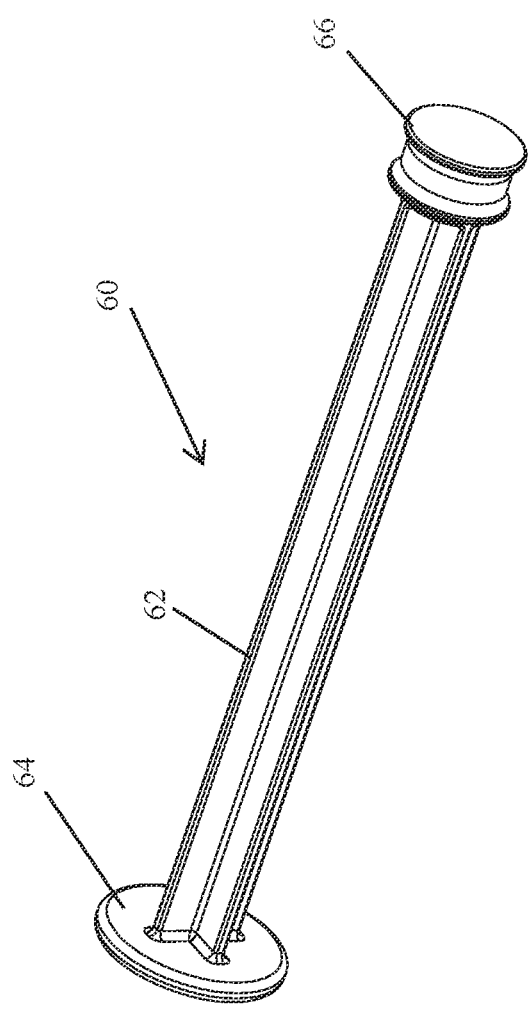
FIG. 5a depicts a ¾ perspective view, and 5b depicts a side view of a secondary plunger assembly, according to an embodiment of the invention.
Figure 5B:
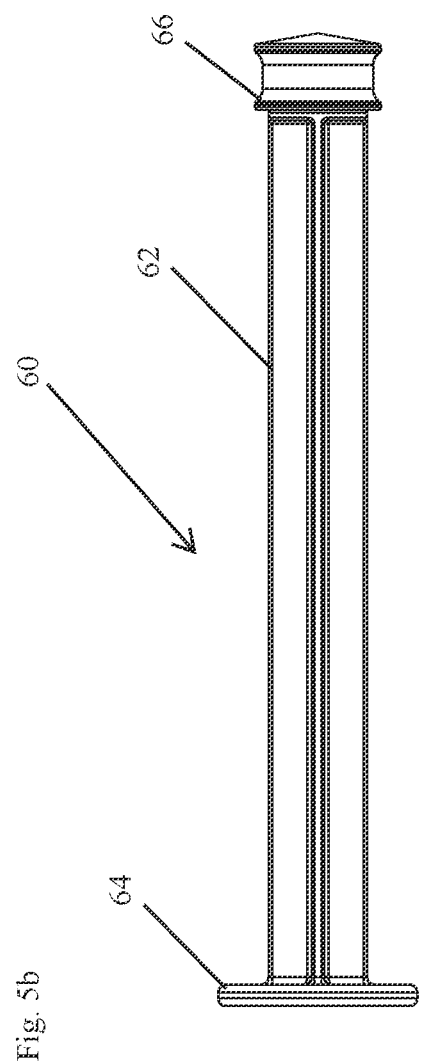

With reference to the FIGS. 2a and 2b, the plunger assembly 10 provides a primary plunger assembly 40, and a secondary plunger assembly 60. The primary plunger assembly 40 is illustrated in detail in FIGS. 4a and 4b, showing opposing perspective views of an exemplary plunger assembly 40. Details of the secondary plunger assembly 60 are illustrated in FIGS. 5a and 5b, depicting a perspective view and side view, respectively.

Figure 1B:
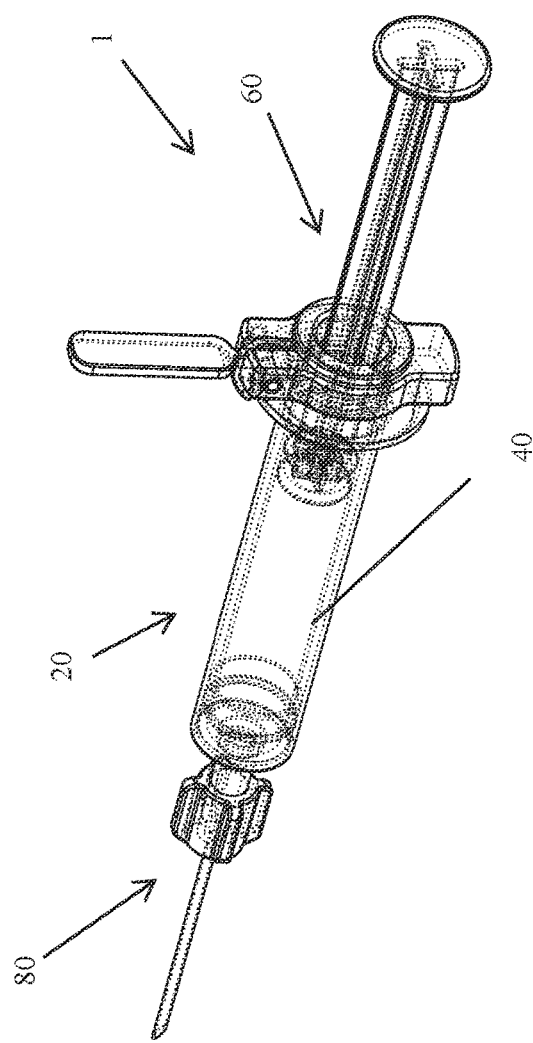

As shown in the assembled view of FIGS. 1a and 1b, the primary plunger assembly 40 is configured to fit concentrically within the interior chamber 22 of the syringe body 20, passing through primary plunger opening 25 and may be advanced distally into the syringe body 20. The secondary plunger assembly 60 is configured to fit concentrically within the interior of the primary plunger assembly 40, as will be discussed. The primary plunger assembly 40 is configured to slidingly move within an interior volume of the syringe barrel 20 and define a first fluid chamber 29 corresponding to the portion of the interior chamber 22 of the syringe body that is positioned distal to the primary piston 46 provided at the distal end of the primary plunger barrel 41, when positioned directed distally through the primary plunger opening 25 into the interior chamber 22. The secondary plunger assembly 60 is configured to slidingly move within an interior volume of the primary plunger assembly 40, as will be discussed.

The primary plunger assembly 40 provides a plunger barrel 41, a primary piston 46 having a valve 47, a collar 48 having a secondary flange 44 and a lock assembly 52.

The plunger barrel 41 provides a hollow, tubular structure. As with the syringe barrel 21, the primary plunger barrel 41 has an annular wall extending generally the length of the primary plunger assembly 40, and having an internal surface defining a secondary interior chamber 42, and has an external surface. When aligned over the longitudinal axis X, at least a portion of the plunger barrel 41 is configured to concentrically fit within the interior chamber 22 of the syringe barrel 21 of the syringe body 20, such that the plunger barrel 41 can slidingly be advanced or retracted within the interior chamber 22. Necessarily, the radial dimension of the barrel 41 of the primary plunger assembly 40, when measured to across the exterior dimensions, is less than the radial dimension of the interior dimensions of the barrel 21 of the syringe body 20, such that the plunger barrel 41 will fit within the tubular barrel 21 of the syringe body 20. The proximal end of the plunger barrel 41 is provided with a secondary plunger opening 43, for receiving the secondary plunger assembly 60 therethrough. The primary plunger barrel 41, at the proximal end, is provided with a collar 48. The collar 48 may be integral with the primary plunger barrel, or may be mechanically secured thereto. At the distal portion of the barrel 41, there is provided a primary piston 46 arranged concentrically around the distal portion of the barrel 41. The distal end of the primary plunger barrel 41 is selectively, or at least temporarily sealed with a valve 47.

The primary plunger barrel 41 may be the same, or different material from the syringe body barrel 21. In an embodiment, the primary plunger barrel may be of any suitable construction, including polymer, glass, and metal, or combinations thereof.

The collar 48 is positioned at, or near, the proximal end of the primary plunger barrel 41, and is positioned about the exterior surface of the primary plunger barrel 41, or forming the distal end thereof. The collar 48 may provide a secondary flange 44, in the form of a radially protruding portion that allows the user to place one or more fingers against for manipulating the movement of the plunger assembly 10, in a manner similar to that discussed above. The collar 48 may also provide the lock assembly 52, as illustrated. At the juncture of the collar to the exterior of the primary plunger barrel 41, the collar on a distal face may provide a recess 50 into which a biasing device 51 may protrude therefrom. The biasing device 51 may be positioned about the exterior of the primary plunger barrel 41, and extending distally from the distal face of the collar 48. The biasing device may be compressed and caused to fit within the recess 50, which may be an annular recess, as will be discussed. In an embodiment, the biasing device 51 may be any suitable compressible and resilient component. As shown in FIGS. 4a and 4b, the biasing device 51 may be provided as a spring, such as the coil spring depicted, having a proximal end fitted within the recess 50, and a distal end that, while in an uncompressed state, is extended at least partly along the length of the primary plunger barrel 41. One skilled in the art will recognize that any suitable resiliently compressible component may be provided, such as wave washer, elastomeric sponge, or elastomeric mesh member, or a resiliently compressible self-expanding mesh structure, such as a helically wound braid, similar to structures known from expandable stents, or finger trap toys. When the biasing device 51 is caused to be compressed, such as when the primary plunger 40 is advanced into the syringe body 20, increasing portions of the biasing device 51 may be received within the recess 50. In an embodiment, where the primary plunger 40 is fully advanced into the syringe body 20, such that the distal end of the primary piston 46 is advanced as far as possible towards the distal wall 23 at the distal end of the syringe body, the biasing device 51 may be caused to be fully received within the recess 50, and is compressed between the collar 48 and the flange assembly 24 as they are approximated together (as depicted in FIG. 6c). In an embodiment, where the biasing device 51 is a coiled spring, the recess 50 may be an annular recess that can receive the compressed coiled spring entirely within the recess 50. The proximal end coil of the coiled spring of such a biasing device would be providing an overcomeable urging force against the containing face of the recess, and the distal end coil of the coiled spring of such a biasing device 51 would be urged against the proximal face of the flange assembly, or the syringe body 20; such that the compressed biasing device 51 seeks to resiliently return to an uncompressed state.

The collar 48 may be the same or different material from the tubular body 41 of the primary plunger assembly. The collar may be mechanically secured to the proximal end of the tubular body 41 in any suitable manner, including through the use of adhesives, fasteners, threaded engagement, friction fit, welding, or by virtue of being integrally formed. In an embodiment, the collar assembly 48 is metal.

The primary piston 46 may be a protruding portion extended about the circumference of the distal portion of the plunger barrel 41. Thus, the exterior dimensions of the primary piston 46 may be greater than those of the primary plunger barrel 41. The primary piston 46 provides a scaled fit against the interior dimensions of the inner surface of the tubular barrel 21 of the syringe body 20.

In an embodiment, the primary piston 46 may be a resilient material that, as the primary plunger 40 is inserted through the primary plunger opening 25 of the syringe body 20, the primary piston 46 is caused to conform against the interior surface of the tubular barrel 21 of the syringe body 20. In another embodiment, the primary piston provides at least one sealing portion extending around the primary piston to create the seal against the interior surface of the tubular barrel. In an embodiment, the primary piston has one or more protruding O-ring portions that are caused to deform and seal against the interior surface as the primary piston is introduced into the interior chamber 22. In another embodiment, the primary piston 46 is formed as the end of the plunger barrel 41 and is dimensioned to seal against the interior surface of the tubular barrel 21 of the syringe body 20.

In any of the embodiments, advancement of the primary plunger assembly 40 into the interior chamber 22 of the syringe body 20 will urge the flow of fluid within the interior chamber 22, specifically within the first fluid chamber 29, distally through the lumen of the needle hub 30, and optionally through the needle 84 of the needle assembly 80, if present. Conversely, retraction of the primary plunger assembly 40, when urged proximally to slide within the interior chamber 22 of the syringe body 20 may draw fluid into the interior chamber 22 through the needle hub 30, and optionally through needle assembly 80. As the primary plunger assembly 40 forms a fluid tight seal when inserted into the syringe body 20, and where the valve 47 is not open for fluid flow therethrough, the volume of the interior chamber 22 that is distal to the primary piston 46 will define first fluid chamber 29. In an embodiment, where the primary plunger 40 is fully advanced into the syringe body 20, such that the distal end of the primary piston 46 is advanced as far as possible towards, and abuts against the distal wall 23 at the distal end of the syringe body 20, the biasing device 51 may be caused to be fully received within the recess 50, and the volume of the first fluid chamber 29 approaches, or is substantially zero, as the primary piston 46 displaces all, or nearly all fluid from within the inner chamber 22, leaving only a minimal amount, which may be confined to the lumen of the needle hub 30, and not contributing to the volume remaining within the interior chamber 22, as depicted in FIG. 6c.

The valve 47 is positioned at the distal face of the primary plunger assembly 40 and may form a distal face to the piston 46 of the primary plunger assembly 40. The valve 47 may serve to provide a selectively sealed portion of the distal end of the secondary chamber 42. In an embodiment, the valve 47 is a resilient sealing device, such as a slit valve, or a variation thereof, such as a cross-slit valve, or a duck-bill valve where one-way fluid flow is suitable. The valve 47 may alternatively be a frangible seal that remains sealed until a rupture pressure is provided to the secondary interior chamber 42 that causes a rupture of the frangible seal, and allows release of some or all of the contents of the secondary chamber through the valve 47. As shown in FIG. 4a, the valve 47 in an exemplary embodiment is a resilient valve, that in an ordinary state remains closed, but can be urged to open, for example, where the pressure within the secondary chamber 42 exceeds the pressure in the primary chamber 22, fluid may pass through the valve 47, and pass from the secondary chamber 42 of the primary plunger assembly 40, through the valve 47, and into the first fluid chamber 29. Such a valve 47 embodiment is depicted as a resilient slit valve provided in the closed position in FIG. 10a, and in the open position in FIG. 12, as will be discussed. One skilled in the art will recognize that the valve 47 need not be limited solely to the embodiment depicted in FIG. 10a. Representative alternative embodiments of valves are depicted in FIG. 10b, as will be discussed. It is contemplated that in any of the embodiments, the discharge of fluid through the valve may optionally provide turbulent flow and/or swirling flow, and thus may optionally promote fluid mixing as the secondary interior chamber is emptied, as will be discussed.

The lock assembly 52 provides a selectively engageable locking means, that when engaged, will serve to secure the position of the primary plunger assembly 40 relative to the position of the syringe body 20. In an embodiment, the lock assembly 52 may be engaged to prevent sliding movement of the primary plunger assembly 40 and retain the position of the primary plunger assembly fully advanced in a distal direction within the syringe body 20, such that the primary piston 46 will be urged against the distal wall 23 of the syringe body 20. In an exemplary embodiment, the lock assembly 52, when engaged, is configured to maintain the biasing device in a fully compressed state, with the biasing device entirely received within the recess 50.

As illustrated in FIGS. 4a and 4b, and in greater detail with reference to FIGS. 6a, 6b, and 6c, the lock assembly may be provided as part of the collar 48 and may be positioned generally radially opposite the secondary flange 44. The lock assembly 52 generally provides an actuator 54, which may be a lever, and a pivot body 56 pivotably secured to a pivot mount 58 of the collar 48, by insertion of a pivot pin 55 directed through both the pivot mount and the pivot body. The lock assembly 52 further provides a latch 57 having a catch recess 59 that can be selectively engaged with the catch 26 of the flange assembly 24 provided on the syringe body 20. The catch recess 59 provides an internal aspect that generally conforms to the exterior surface profile of the catch 26, such that the catch can be securely retained within the catch recess 59 of the lock assembly 52.

The pivot body 56 may be a rotatable body having a through-hole, oriented perpendicular to the longitudinal axis X. The pivot mount may be a pair of outward extending bodies provided on the collar 48, each having an aligned through hole therethrough, and the pivot body may then be positioned between the bodies of the pivot mount. In the embodiment shown, the pivot pin 55 is a hinge pin inserted through the first extending body of the pivot mount, through the through hole of the pivot body 56, and then through the second extending body of the pivot mount 58. However, one skilled in the art would appreciate that the lock assembly 52 could be substituted with other known mechanical devices that function similarly to embodiment shown, including a living hinge, a toggle hinge or other known clasping devices. The width dimension of the pivot body (measured perpendicular to the longitudinal axis X), is smaller than the gap provided between the bodies of the pivot mount 58, such that the pivot body maybe pivoted by movement of the actuator 54 (e.g., lever), while the pivot body 56 is secured by the pivot pin 55. As shown, in FIGS. 4a and 6a, the pivot body 56 has an actuator 54 extending away from the pivot pin in a first direction, and a latch 57 extending away from the pivot pin 55 in a second direction. As illustrated in the FIG. 6C, the lock assembly 52, when engaged, provides the actuator extending generally perpendicular to the longitudinal axis X, and the latch extending generally parallel to the longitudinal axis X. One skilled in the art will recognize that alternative designs are possible, and still fall within the spirit of this disclosure. The length of the actuator 54, when measured from the center of the pivot pin 55 to the end of the actuator 54 is generally longer than the corresponding length of the latch 57, where the additional length of the actuator allows for the user to rely on relatively higher leverage possible through the actuation of the actuator to overcome resistance to release provided through the latch 57, where the catch recess 59 is engaged with the flange catch 26, and may be under tension due to the stored energy retained in the biasing device 51 when compressed. Use and operation of the lock assembly 52 will be described below.

The secondary plunger assembly 60 provides a plunger shaft 62, a pad 64 provided at the proximal end of the plunger shaft, and a secondary piston 66 provided at the distal end of the plunger shaft. The secondary plunger assembly 60 may be of any suitable construction, including polymer, glass, and metal, or combinations thereof. Unlike the previously described primary plunger assembly 40, the secondary plunger assembly 60 provides no interior chamber. Rather as shown in FIG. 2a, the plunger shaft 62 is a generally rigid body that can transmit a force applied to the pad 64, through the secondary plunger shaft and apply the force to the secondary piston 66. The secondary piston 66 may be a conventional plunger piston, as is known with syringes, and will be familiar to those of skill in the art. The secondary piston 66 is dimensioned to form a fluid impermeable seal against the interior surface of the primary plunger barrel 41. In an embodiment, the secondary piston 66 is a resilient material that will be slightly deformed against the interior surface of the plunger barrel 41. Thus, the secondary chamber 42, corresponding to the interior volume of the primary plunger barrel 41, will feature a second fluid chamber 49 when the secondary piston 66 is sealed against the interior of the primary plunger assembly 40, where the secondary fluid chamber is defined at a proximal end by the distal face of the secondary piston 66, and at the distal end of the second fluid chamber 49 by the proximal face of the valve 47, constrained by the interior aspect of the primary plunger barrel 41. Thus, the volume within the second fluid chamber 49 is variable, and changes, depending upon the positioning of the secondary piston 66 within the secondary chamber 42. In an embodiment, the secondary plunger shaft 62 is of a narrower outer dimension (measured perpendicular to the longitudinal axis X) than the similar dimension of the secondary piston 66. The secondary plunger shaft 62 will fit within the primary plunger shaft, with the secondary piston 66 fitting tightly against the interior surface of the primary plunger barrel 41, but still capable of sliding movement to allow actuation of the secondary plunger assembly 60. The distal face of the secondary piston 66 is configured to conform against the proximal face of the valve 47, such that when the secondary plunger 60 is fully advanced into the primary plunger assembly 40, whereupon the secondary piston 66 is advanced as far as possible towards, and abuts against the valve 47 provided at the distal end of the primary plunger assembly 40, the volume of the second fluid chamber 49 approaches, or is substantially zero, due to the secondary piston 66 having displaced all, or substantially all of any fluid from within the secondary chamber 42, as depicted in FIG. 14c.

Use and operation of the syringe assembly 1 is depicted in FIGS. 1a, 1b, and 6a-14c. The syringe assembly is shown in opposite perspective views in FIGS. 1a and 1b, with an exemplary needle assembly 80 provided secured to the distal hub 30 of an exemplary syringe body 20. An exemplary primary plunger assembly 40 is fully advanced into the syringe body 20 and an exemplary lock assembly 52 is depicted as being engaged, by having the actuator 54 rotated into a position, such that the latch is engaged with the catch 26 of the flange 24. An exemplary secondary plunger assembly 60 is depicted only partly inserted into the interior chamber 42 of the primary plunger assembly 40 and having the majority of the shaft 62 of the secondary plunger assembly 60 protruding proximally from the primary plunger assembly. The syringe assembly 1 depicted in FIGS. 1a and 1b, is similarly positioned in the side view and cross section view of FIGS. 6a and 6b, respectively. The syringe assembly 1 is also depicted in FIG. 6b, with the view being provided along the longitudinal axis X, and the needle assembly 80 provided at the front of the depicted end-on view.

As can be seen with reference to FIGS. 1a, 1b, and in cross section view of FIG. 6c, the secondary plunger assembly 60 is concentrically aligned within the interior of the primary plunger assembly 40, which, in turn, is concentrically aligned within the interior of the syringe body 20. All of the secondary plunger assembly 60, primary plunger assembly 40, syringe body 20 and needle assembly 80 are aligned along the longitudinal axis "X", extending through the concentric center of each of the components.

As illustrated in FIGS. 7a and 6b, the lock assembly 52 is engaged, as discussed with reference to FIGS. 7a and 7b. In such a configuration, the biasing device 51 is fully compressed by the flange assembly compressing the biasing device 51 in a proximal direction and urging the biasing device into the recess 50 that is inset into the distal face of the collar 48. The biasing device 51 thus has stored energy within the biasing device, such as where the biasing device 51 is a compressible coil spring, as shown, that seeks to return to an uncompressed state, but is unable to do so due to the lock assembly 52 being engaged, and restraining the collar 48 and flange assembly 24 from separating movement.

As illustrated in the detail view of FIG. 6d, the distal end of the primary plunger assembly 40 is positioned against the distal wall 23 of the syringe body, with the seal 47 positioned immediately adjacent to the lumen of the needle hub 30. Note that there is substantially no volume remaining of the first fluid chamber 29, due to the primary piston being fully advanced into the interior chamber 22 of the syringe body assembly 20.

FIGS. 7a and 7b show the lock assembly 52 securely engaged, with the catch 26 captured within the correspondingly shaped catch recess 59 (as can be seen with reference to 8a) of the latch 57, such that the primary plunger assembly 40 is releasably secured, and unable to slidingly move relative to the syringe body 20. The lock assembly provides the actuator 54, provided here as a lever, that is positioned perpendicular to the longitudinal axis X when the locking assembly 52 is engaged. As shown in FIG. 7b, the latch 57 may be slightly larger than the dimensions of the catch 26 provided on the flange. Ideally, the catch 26 is circular, (as depicted in FIG. 2a) such that the locking assembly 52 can be engaged, irrespective of the rotational positions of the primary plunger assembly relative to the syringe body.

In such a configuration, a user of the syringe assembly 1 may position the distal end of the needle 84 of the needle assembly 80 in a target site, such as tissue to be treated, and may use a first hand to position the syringe assembly 1, and a second hand may either restrain or position the tissue being treated or targeted, or may be manipulating a monitoring device for observing the placement of the needle at the desired location, such as through the use of an ultrasound probe, or other suitable monitoring device. With needle properly positioned, and the second hand remaining in the initial position, the first hand may simply apply pressure to the actuator of the lock assembly to disengage the lock assembly and thereby allow the compressed biasing device to seek to return to an uncompressed state, thereby initiating the automatic aspiration of fluid into the first fluid chamber, as will be discussed. Such automatic aspiration may serve any suitable purpose, including confirming proper placement of the needle tip, where aspiration of fluid upon release of the catch can provide an indication of proper positioning of the tip of the needle in the target area, for example, within a blood vessel, or alternatively providing an amount of fluid automatically aspirated within the interior chamber, such that the aspirated fluid can then receive and/or dilute a second fluid (such as a medication) delivered from the second fluid chamber, as it is passed into and passes through the first fluid chamber, to be delivered to the target tissue.

As illustrated in FIG. 8a and in detail in 8b, the actuator 54 may be actuated, by being urged by the user to an orientation away from perpendicular to the longitudinal axis X, causing the pivot body 56 to rotate about the pivot pin 55 where the pivot body is secured in the pivot mount 58. The rotation of the pivot body 56 in turn frees the catch 26 from being restrained within the latch 57, as the latch is caused to rotate upwards away from the flange assembly 24, upon actuation of the actuator 54. With lock assembly 52 now disengaged, the biasing device 51 seeks to return to a relaxed, uncompressed state.

FIGS. 9a, 9b, and 9c depict the syringe assembly 1 with the lock assembly 52 having been disengaged, and the biasing device 51 being freed from being retained in compression. The lock assembly 52, when placed into a disengaged state, will allow the biasing device 51 to seek to return to a low energy, uncompressed state by urging the primary plunger assembly 40 to slidingly move proximally within the syringe body 20.

As illustrated in FIGS. 9a and 9c, the biasing device 51 has at least 2 coils of the biasing device (where the biasing device is a coiled spring) that extends out from the recess 50 of the collar 48, and pushes against the flange assembly 24 of the syringe body 20, while also pushing against the collar 48 from the end positioned within the recess 50, thereby pushing the collar 48 away from the flange assembly 24 to create an aspiration of fluid at the distal end of the syringe assembly 1. The movement of the primary plunger assembly 40 in a proximal direction, relative to the syringe body 20 will create an aspirating force as the primary piston 46 is caused to move proximally within the interior chamber 22, thereby drawing fluid into the first fluid chamber within the interior of the syringe body, which fluid aspiration may serve to provide a positive location identifier for the needle tip in the target tissue to be treated.

Once the biasing device 51 has returned to a low energy, uncompressed state, it will no longer urge the proximal movement of the primary plunger assembly 40. The extent to which the primary plunger assembly will be urged proximally can be controlled by manipulating the characteristics of the biasing device 51, for example fewer turns to a coiled spring, providing a shorter length of such a biasing device 51 will urge the primary plunger to a lesser extent than would a coiled spring having more coils of equal characteristics (strength, coil spacing/pitch). Additionally, the compression characteristics of the biasing device 51, whether linear, or non-linear compression resistance would allow tailoring of how much of the length of the syringe body 20 that the primary plunger would be retracted proximally in response to the urging of the biasing device. In an embodiment, as depicted in FIG. 9c, the biasing device may only urge the aspiration of fluid by urging the retraction of the primary plunger assembly proximally and creating a first fluid chamber 29 that approximates one quarter or less of the volume of the internal chamber 22 of the syringe body 20. It is contemplated that a biasing device 51 that is of greater length in an uncompressed state, for example, by having more coils and/or larger pitch having a greater distance between adjacent coils, will allow the user to select a biasing device 51 that can be tailored in the distance the primary plunger would be urged proximally, and thereby control the total volume of fluid aspirated upon release of the locking assembly 52, as described herein. Where the biasing device is of a length that approaches the length of the syringe body 20, a syringe assembly that may automatically aspirate an amount of fluid into a first fluid chamber that approaches the entirety of the volume of the interior chamber 22 within the syringe body 20.

While the biasing device 51 is depicted as a coiled spring, it is contemplated that alternative biasing device embodiments are possible, so long as such material or device is capable of being compressed, held for a period of time in the constrained state, and when released from constraint will seek to return to an uncompressed state. In addition to metal and polymer springs, such as coiled or mesh springs, it is contemplated that a resilient, elastomeric sponge material may be provided as a biasing device suitable for use in the invention.

In an embodiment, some or all of the interior chamber 22 of the syringe barrel a may serve as the first fluid chamber 29, the extent of which is controlled by urging the primary plunger assembly to advance or retract within the syringe barrel 21 in a desired amount. Once the biasing device 51 is no longer applying an urging force to the collar 48 of the primary plunger, and urging it in a proximal direction, should additional volume be desired to be aspirated, the primary plunger assembly 40 may be urged in a proximal direction further, until the primary piston 46 is nearly at the opening 25 of the syringe barrel 21. Should additional volume be sought to be aspirated, the secondary plunger assembly 60 is urged in a proximal direction, sliding within the barrel 41 of the primary plunger assembly, to aspirate fluid into the secondary chamber 41, where the fluid is drawn into the second fluid chamber 49. Thus, either or both of the primary and secondary plunger assemblies are capable of being urged distally and proximally, with the movement controlled using the techniques known with other syringes to advance or retract each of the plungers.

The second plunger assembly 60 may be urged proximally to draw additional fluid into the syringe assembly 1, where the continued aspiration of fluid results in an increase of fluid volume within the secondary fluid chamber 49. Deploying the syringe assembly 1 in this manner would allow the user to aspirate a volume of fluid that may exceed the total volume of the interior chamber 22 of the syringe barrel 21, where the user is relying on the volume provided within the secondary interior chamber 42 of the primary plunger barrel 41 as an additional reservoir for receiving fluid therein, in addition to the reservoir provided by the interior of the syringe barrel 21. It is contemplated that this use may be possible whether the secondary fluid chamber 49 initially contains a fluid for delivery, such as a medicament, or not.

The urging by the biasing device 51 of the primary plunger assembly 40 to move in the proximal direction, relative to the syringe body 20, and drawing fluid in through the needle hub 30 into the interior of the syringe body 20 will result in the aspirated fluid remaining within the first fluid chamber 29, as the valve 47 will be in a closed state, as depicted in FIG. 10a. In an embodiment, where the proper placement of the needle assembly 80 of the syringe assembly 1 may be confirmed by aspiration of fluid into the interior of the syringe body; the user may then initiate the delivery of a second fluid from the secondary fluid chamber 49, as will be discussed. Alternatively, where the aspiration is not provided as a location identifier, but rather to provide a diluent fluid within the first fluid chamber, the delivery of the second fluid from the second fluid chamber 49 may be similarly initiated, as discussed below.

With reference to FIGS. 11a, 11b, and 11c, a force applied to the pad 64 of the secondary plunger assembly 60 will result in the secondary piston 66 being advanced within the interior of the primary plunger assembly 40, increasing the pressure within the second fluid chamber 49 and urging the ejection of the fluid within the second fluid chamber 49. The passing of the second fluid from the second fluid chamber 49 as a result of increased relative pressure within the second fluid chamber 49 compared to that in the first fluid chamber 29, is depicted with reference to FIG. 12, where the valve 47 has a slit in the resilient valve body that is opened to allow the passage of fluid therethrough. Upon equalization of the pressures in the first and second fluid chambers 29, 49, the valve 47 will resiliently return to the sealed state, depicted in FIG. 10a.

It is contemplated that the fluid within the secondary chamber 42 of the primary plunger assembly 40, and contained within the second fluid chamber 49, may be a second fluid, such as a medicament, that had been initially provided within the second fluid chamber 49, or was introduced by the user into the second fluid chamber 49, such as may be possible by maintaining the locking assembly 52 in an engaged state, and urging the secondary plunger assembly in a proximal direction to draw a fluid into the syringe assembly 1, as the primary plunger assembly 40 is constrained from movement, the vacuum created within the second fluid chamber 49 by retraction of the secondary piston 66 would cause the aspiration of an amount of fluid through the needle hub 30, and pass through the valve 47 in a proximal direction to introduce the aspirated liquid into the second fluid chamber 49. In this manner, the syringe assembly 1 may be pre-loaded with a desired second fluid contained within the second interior chamber 42 of the primary plunger assembly 40, such as a medicament, that may later be delivered into a target site, using the teachings herein. Alternatively, it is contemplated that the fluid within the second fluid chamber 49 may be the same composition as provided within the first fluid chamber 29. In either event, urging the secondary plunger assembly distally will cause the fluid within the second fluid chamber 49 to be expelled out through the valve 47 and passing into the first fluid chamber 29. As liquid is incompressible, the volume of fluid passing through the valve 47 will result in the displacement of the fluid within the first fluid chamber 29, which would be ejected out the distal end of the syringe assembly 1. It is recognized that some mixing may occur within the first fluid chamber 29. The effect of mixing within the first fluid chamber 29 may be enhanced by providing one or more slit seals that will encourage directional flow as fluid is ejected from the second fluid chamber 49 into the first fluid chamber 29. It is contemplated that the valve may provide one or more resiliently openable ports, similar to the slit depicted, only having an angled passage therethrough. Such an angled slit would encourage a swirling flow within the first fluid chamber 29 as the secondary plunger assembly 60 is actuated in a distal direction to pass the second fluid through the angled passage provided in the valve 47, where the directional flow would swirl or turbulently mix with the fluid within the first fluid chamber 29.

FIG. 10b depicts a perspective view of the primary plunger assembly, showing the primary piston and valve having one or more directional valve slits to encourage a directional ejection of fluid as the secondary plunger assembly is advanced distally. Providing multiple directional slits in the valve would contrast with the valve 47 depicted in FIG. 10a, where it is provided with a single slit opening, and is depicted in FIG. 12 in an open state, allowing fluid to pass through the open slit of the valve 47, in a direction generally parallel to the longitudinal axis. Referring to FIG. 10b, alternative valve embodiments are shown, depicted as having a plurality of directional slit openings, as can be seen with reference to the exemplary varieties of slits provided in the alternative embodiments of the valves, depicted as representative alternative embodiments of valves 47', 47", 47''' and 47''''. As shown, each of the alternative representative valves of FIG. 10b feature a plurality of shaped slits that will open in a manner that encourages non-axial, directional flow from the respective slit(s). While FIG. 10b depicts alternative embodiments having three slits, it is contemplated that a different number of directional slits may be provided. For example, in FIG. 10b, the valve 47' includes three "v" shaped slits arranged circumferentially around the central axis. In the embodiment of the valve 47", three slit openings are provided, each one being a "v" shape with uneven lengths. In the embodiment of the valve 47''', a plurality of shaped slits are provided circumferentially around the central axis, with each slit being an "L" shape, providing uneven lengths for the portion of the "L" slit, that meet at a right angle. In the embodiment of the valve 47'''', a plurality of shaped slits are provided circumferentially around the central axis, with each slit being provided generally in a "U" shape. Each of the alternative slits of valves 47', 47", 47''', and 47'''' will encourage directional flow by virtue of the valve material distorting to open the slits as injection pressure is applied to the secondary plunger assembly 60, and causing each of the alternative slits to bend along a hinge line, corresponding to an imaginary line positioned extending between the ends of the slit(s), and thereby allowing the deflection of the valve material positioned within the interior of the V, L, or U shaped slit, or in other shapes, to the inside of the slit, and thus forming a directional opening that will encourage directional, and non-axial exit streams as the fluid is ejected through slits in representative valve embodiments of FIG. 10b. The non-axially directed, directional streams would then result in a mixing and/or swirling effect, for example, as the directional streams encounter the interior surface of syringe barrel 21 within the interior chamber 22. It is contemplated that any number or combination of directional or non-directional valve slits may be provided and need not be limited solely to the depicted representative embodiments. One skilled in the art will recognize that alternative slit shapes (e.g., rounded directional slits such as a "C" shape) may be provided to similar effect, in that a mixing effect can be achieved within the first fluid chamber 29 of the syringe body 20 (of FIG. 9c). In an embodiment, the valve 47 may provide at least one slit, and may provide a plurality of slits, where each of the slits are symmetrically positioned, when viewed along the longitudinal axis, as depicted in the various valve embodiments depicted herein.

Figure 19A:
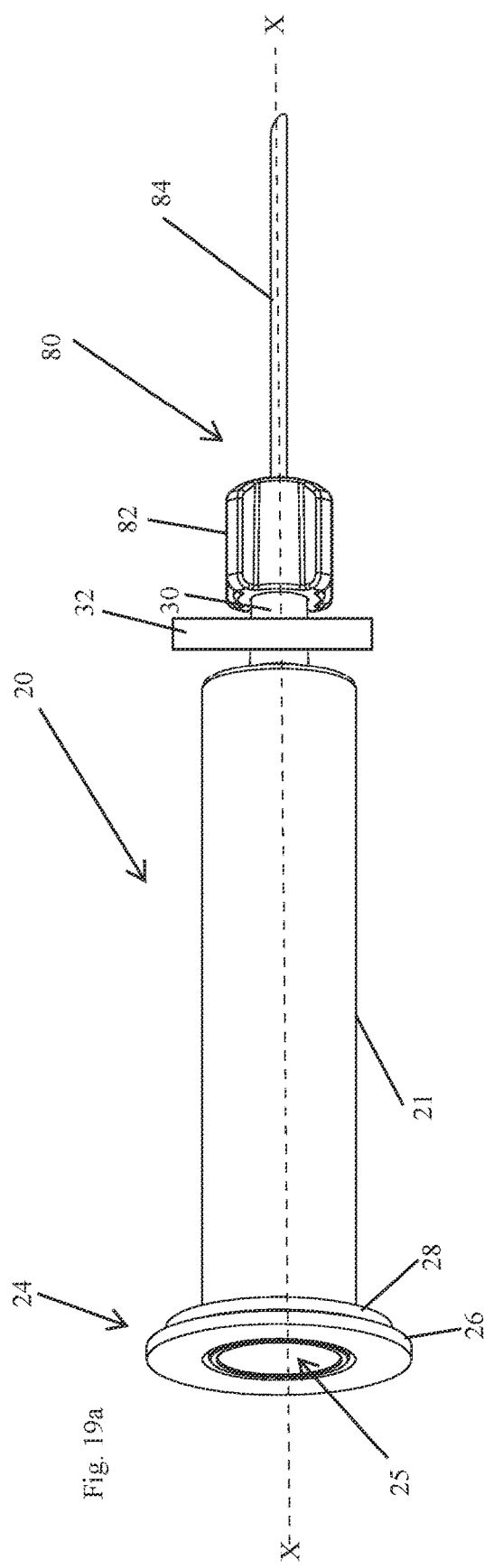
FIGS. 19a and 19b depict an isolated view of the syringe barrel and needle assembly having a selectively closable valve in the needle hub, provided in a side perspective view, and cross-section view, respectively, according to an embodiment of the invention.
Figure 19B:
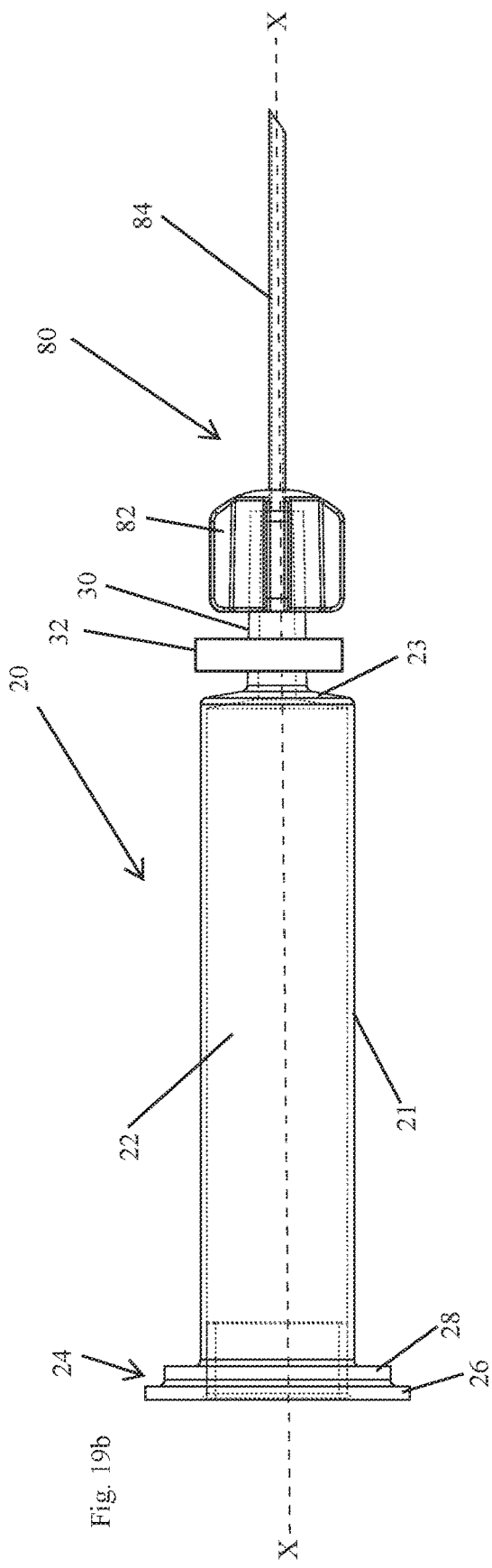

In an embodiment, mixing of the fluid within the first fluid chamber 29, with a liquid from the secondary fluid chamber 49 may further be facilitated by providing a selectively closed end of the syringe body 20. With reference to FIGS. 19a and 19b, there is provided a view of a syringe body 20, similar to that depicted in FIGS. 3a and 3b, only modified to include a representation of a selectively actuatable distal end valve 32, shown here positioned to selectively allow or block the passage of fluid through the needle hub 30. It is contemplated that the valve 32 need not be positioned in the needle hub where shown, and may instead be a valve hub that can be attached to the needle hub 30 (e.g., by luer fitting), and which may in turn receive the needle assembly 80. Referring to the embodiment depicted in FIGS. 19a and 19b, closure of the distal end of the first fluid chamber 29 may be achieved by providing a selectively actuatable distal end valve 32 provided at or near the needle hub 30. Such a distal end valve may selectively seal the distal end of the primary fluid chamber 49, and create a closed chamber that improves mixing within the first fluid chamber as the secondary plunger assembly is advanced, forcing fluid from the secondary fluid chamber 49 through the valve 47, or any of the alternative embodiments, and passing into the first fluid chamber 29, to mix with the volume therein. As liquids are generally incompressible, advancement of the secondary plunger assembly, so long as the distal end valve 32 remains closed, would result in the primary plunger assembly being urged proximally in a proportional amount to offset the fluid delivered from the secondary fluid chamber 49. Reciprocation of the secondary plunger assembly may improve mixing of the fluid within the plunger assembly. Once the user desires to inject fluid from the first fluid chamber 29, the distal end valve 32 may be selectively opened to allow fluid flow therethrough as the plunger assembly is advanced distally to urge the fluid to exit from the first fluid chamber 29 through the open distal end valve 32, if present, and to a target site. It is recognized that any suitable valve arrangement may be utilized to selectively seal the distal end of the syringe body, such as a ball valve, a guillotine valve, etc. Selection of a suitable valve configuration, and operation thereof, for selectively closing or opening flow into, or out from, the syringe body 20 and the distal hub 30 will be familiar to those of ordinary skill in the art.

FIG. 13a, b, and c depict the syringe assembly 1, where the continued advancement of the secondary plunger assembly 60 has continued to the point that the secondary piston 66 has encountered the distal end of the primary plunger assembly 40, and the second fluid chamber 49 has been reduced to substantially zero volume, as all of the second fluid has been expelled from the second fluid chamber. With the secondary piston urged against the proximal face of the valve 47, the resilient seal will return to a closed state, as depicted in FIG. 10a, as there is no relatively elevated pressure within the second fluid chamber 49, compared to the relative pressure within the first fluid chamber 29. As depicted in FIGS. 13a and c, the biasing device 51 may just be in contact with the proximal face of the flange assembly.

Continued pressure applied to the pad 64 of the secondary plunger assembly 60 will result in the plunger assembly 10 being further advanced in the distal direction, compressing the biasing device 51, such that the biasing device may be received within the recess 50, as illustrated in FIGS. 14a and c. As depicted, the volume of fluid remaining within the first fluid chamber 29 will be expelled through the needle hub 30 and optional needle assembly 80 as the plunger assembly 10 is advanced within the syringe body 20, until such a point as the primary piston 46 abuts against the distal wall 23 of the syringe barrel 21, and reducing the volume of the first fluid chamber to substantially nothing as substantially all of the fluid is expelled from the interior of the syringe body 20, with only a small amount of fluid remaining within the lumen of the needle hub 30 and needle assembly. Should there be a need to minimize dead volume remaining within the needle, it is known to provide a piston of the plunger assembly having a protruding portion that substantially conforms to the volume and shape of the lumen within the needle hub 30, as will be familiar to those of ordinary skill in the art.

With substantially all of the fluid expelled from both second fluid chamber 49, and the first fluid chamber 29, and with the biasing device 51 compressed as the primary plunger assembly 40 is urged distally towards the syringe body 20, as depicted in FIG. 15*a* and in detail in FIG. 15 *b*, the locking assembly 52 may be in position such that it can again be caused to become engaged. As illustrated in FIGS. 16*a* and in greater detail in FIG. 16*b*, the locking assembly may be reengaged in order to restrain the relative positions of the primary plunger assembly 40 within the syringe body 20. Additionally, as the secondary plunger assembly 60 is retained within the primary plunger assembly, the secondary plunger assembly will not move unless acted upon by the user. Thus, absent intervention from the user, engagement of the locking assembly 52 will secure the plunger assembly 10, relative to the syringe body 20. The locking assembly 52 may be reengaged by urging the actuator 54 to return to the initial locked orientation, thereby rotating the pivot body 56 about the pivot pin 55, and urging the latch 57 to pivot downwards and reengage the catch 26 of the flange assembly 24, such that the catch 26 is received within the catch recess 59. With the locking assembly 52 engaged, the urging of the biasing device 51 will be restrained from becoming effective, and the relative positions of the plunger assembly 10 and the syringe body 20 will be maintained, unless the user opts to either release the locking assembly 52, or retract the secondary plunger assembly 60, whereupon the aspiration into the second fluid chamber 49 may be caused to occur.

Figure 17:
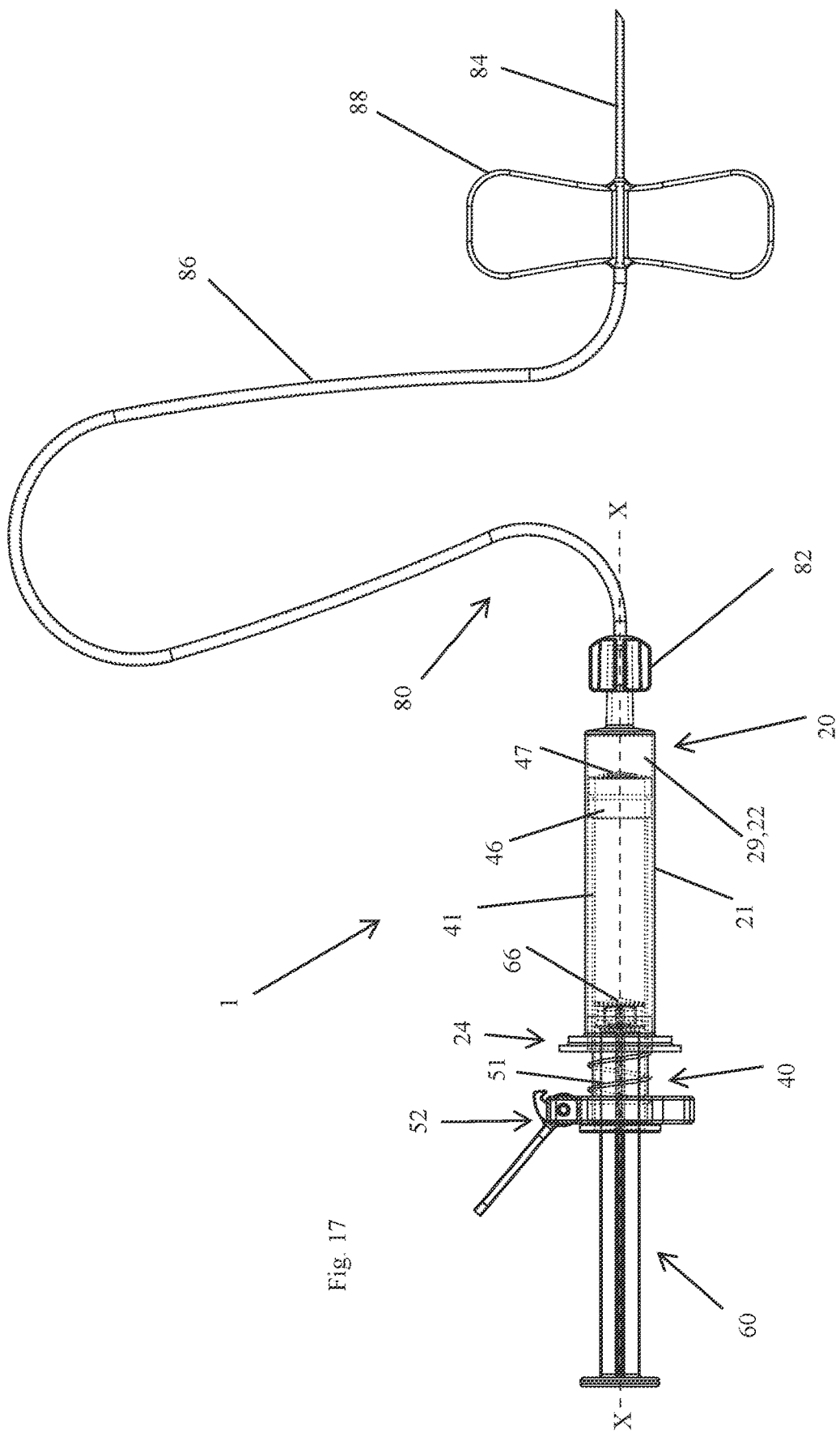

In an exemplary embodiment, the syringe assembly 1 may be utilized with a needle assembly 80 that provides a length of a lumen positioned between the connector fitting 82, and a needle 84. As illustrated in FIGS. 17 and 18, the depicted embodiment of the syringe assembly 1 features a flexible tubing having a lumen therethrough provided as part of the needle assembly 80. The depicted embodiment provides a winged infusion set with a connector fitting 82, a flexible infusion tubing 86, the infusion wings 88, and terminating with a needle 84, such as an IV needle. It is recognized that the syringe assembly 1 may similarly be deployed for use with a device without having a needle end, and may be connected at the needle hub 30 to a suitable connector fitting provided on any suitable lumen device, including, but not limited to, a catheter, hollow guidewire, or cannula, so long as provided with an open distal end that allows delivery and aspiration of a fluid therethrough in response to actuation of the plunger assembly 10, for example, as illustrated in FIGS. 17 and 18. Such embodiments may be utilized by actuating one or more of the plunger assembly 10 components according to any of the teachings herein.

Many other embodiments are possible within the scope and spirit of the invention. Therefore, more or less of the aforementioned components can be used to conform to that particular purpose. It is, therefore, intended that the foregoing description be regarded as illustrative rather than limiting, and that the scope of the invention is given by the appended claims together with their full range of equivalents.

What is claimed is:

1. A syringe assembly comprising:
   a syringe body having a hollow syringe barrel, a needle hub provided at a distal end of the hollow syringe barrel, and a flange assembly provided at a proximal end of the syringe body; and
   a plunger assembly having a primary plunger assembly and a secondary plunger assembly,
      the primary plunger assembly having a hollow plunger barrel, a collar provided at a proximal end of the hollow plunger barrel, a biasing device, and a valve provided at a distal end of the hollow plunger barrel, with the hollow plunger barrel being configured to be received and slidingly move within the hollow syringe barrel, and the biasing device being configured to urge the hollow plunger barrel along a longitudinal axis extending through the center of the syringe body in a proximal direction relative to the hollow syringe barrel, and
      the secondary plunger assembly configured to be received and slidingly move within the hollow plunger barrel.

2. The syringe assembly of claim 1, wherein the flange assembly includes a catch and a shoulder.

3. The syringe assembly of claim 2, wherein the catch protrudes out from the hollow syringe barrel perpendicularly to the longitudinal axis.

4. The syringe assembly of claim 2, wherein the shoulder is provided distal to and adjacent to the catch and joins the flange assembly to the syringe barrel.

5. The syringe assembly of claim 2, wherein the primary plunger assembly has a locking assembly, and at a distal end of the primary plunger assembly there is provided a primary piston and the valve is a resilient slit valve.

6. The syringe assembly of claim 5, wherein the valve has at least one valve slit configured to provide a non-axial, directional stream when opened.

7. The syringe assembly of claim 6, wherein the valve is normally closed, but will resiliently open in response to the sliding movement of the secondary plunger assembly within the hollow plunger barrel.

8. The syringe assembly of claim 5, wherein the locking assembly provides a pivoting body with an actuator and a latch, the pivoting body pivotably mounted to the collar.

9. The syringe assembly of claim 8, wherein the actuation of the actuator in a first direction will engage the latch with the catch to secure the primary plunger assembly relative to the syringe body.

10. The syringe assembly of claim 9, wherein when the latch is engaged with the catch, the biasing device is compressed between the flange and the collar that are positioned in close proximity.

11. The syringe assembly of claim 10, wherein the collar further provides a recess to receive the biasing device therein when compressed.

12. The syringe assembly of claim 10, wherein the actuation of the actuator in a second direction will disengage the latch with the catch to allow sliding movement of the primary plunger assembly relative to the syringe body, when the biasing device is allowed to transition to an uncompressed state.

13. The method of delivering a medicament with a syringe assembly, the method comprising:
   a. providing a syringe assembly having
      a syringe body with a first internal chamber,
      a needle assembly with a lumen therethrough and in fluid communication with the first internal chamber, a primary plunger assembly with a second internal chamber having a second fluid therein and having a valve located at the distal end of the second internal chamber, the valve being in fluid communication with the first internal chamber, the primary plunger assembly configured to slidingly fit within the first internal chamber, and a secondary plunger assembly configured to slidingly fit within the second internal chamber, and having a biasing device provided in a temporarily compressed state positioned between the primary syringe assembly and the syringe body while a lock assembly remains engaged;

b. directing a tip of the needle assembly positioned on a distal end of the syringe assembly to a target location;

c. disengaging the lock assembly, whereupon the biasing device transitions from a first state characterized by the biasing device being compressed to a second, and uncompressed state, simultaneously urging a proximal directed movement of the primary plunger assembly within the first internal chamber of the syringe body, and drawing a first fluid into a first fluid chamber within the first internal chamber, and thereby providing confirmation of the location of the tip of the needle at the target location; and d. advancing the secondary plunger assembly in a distal direction to deliver an amount of the second fluid from the second internal chamber through the valve and into the first internal chamber, and further through the lumen of the needle assembly to the target location.

14. The method of claim 13, wherein the second fluid contains a medicament.

15. The method of claim 14, wherein the biasing device is a resilient coiled spring positioned between a collar provided at the proximal end of the primary plunger assembly, and a flange assembly provided at a proximal end of the syringe body, the coiled spring being wound about a portion of the primary plunger assembly.

16. The method of claim 15, wherein the coiled spring is configured to be releasably compressed into a coiled state having stored energy therein, and the coiled spring is configured to be received within a recess in the collar.

17. The method of claim 16, wherein the flange assembly provides a circular catch and shoulder, the shoulder joining the flange assembly to the syringe body, and the circular catch protruding radially out from the shoulder.

18. The method of claim 13, further comprising the steps of:

e. advancing the primary plunger assembly in a distal direction to compress and return the biasing device to the first state; and f. engaging the lock assembly, while maintaining the biasing device in the first state.

* * * * *